United States Patent
Peng et al.

(10) Patent No.: US 11,504,428 B2
(45) Date of Patent: Nov. 22, 2022

(54) PHOTOSENSITIZER AND DERIVATIVES AND APPLICATION THEREOF

(71) Applicants: DALIAN UNIVERSITY OF TECHNOLOGY, Liaoning (CN); DALIAN CHROMAS BIOSCIENCE CO., LTD, Liaoning (CN)

(72) Inventors: Xiaojun Peng, Liaoning (CN); Mingle Li, Liaoning (CN); Jiangli Fan, Liaoning (CN); Qichao Yao, Liaoning (CN); Jianjun Du, Liaoning (CN); Saran Long, Liaoning (CN); Jingyun Wang, Liaoning (CN)

(73) Assignees: DALIAN UNIVERSITY OF TECHNOLOGY, Liaoning (CN); DALIAN CHROMAS BIOSCTENCE CO., LTD, Liaoning (CN)

( * ) Notice: Subject to any disclaimer, the term of this patent is extended or adjusted under 35 U.S.C. 154(b) by 282 days.

(21) Appl. No.: 16/633,087

(22) PCT Filed: Nov. 24, 2017

(86) PCT No.: PCT/CN2017/112765
§ 371 (c)(1),
(2) Date: Jan. 22, 2020

(87) PCT Pub. No.: WO2019/024339
PCT Pub. Date: Feb. 7, 2019

(65) Prior Publication Data
US 2021/0030873 A1 Feb. 4, 2021

(30) Foreign Application Priority Data
Aug. 4, 2017 (CN) .......................... 201710660846.1

(51) Int. Cl.
*A61B 5/00* (2006.01)
*A61B 8/00* (2006.01)
(Continued)

(52) U.S. Cl.
CPC ........ *A61K 41/0057* (2013.01); *A61K 31/405* (2013.01); *A61K 31/4188* (2013.01);
(Continued)

(58) Field of Classification Search
CPC ............ A61K 41/0057; A61K 31/5415; A61K 31/55; A61K 47/55; A61K 47/551;
(Continued)

(56) References Cited

U.S. PATENT DOCUMENTS 4,962,197 A   10/1990   Foley et al.
5,832,931 A * 11/1998   Wachter ............... A61K 41/008
                                                          600/300
(Continued)

FOREIGN PATENT DOCUMENTS

CN   103360385 A   10/2013
WO       0183621 A2   11/2001
WO   2009137062 A2   11/2009

OTHER PUBLICATIONS

Xu, Jing, "Development of Phenoxazinium Chalcogen Analogues as Photosensitizers' Design, Synthesis and Property Study", Science —Engineering (A), China Master's Theses Full-Text Database, May 15, 2014.
Oliver, J.K. et al., "In Vitro Optimization of EtNBS-PDT Against Hypoxic Tumor Environments with a Tiered, High-Content, 3D Model Optical Screening Platform", Molecular Pharmaceutics, 9(11), Sep. 2012, pp. 3171-3182.
Oliver, J.K. et al., "In Vitro Optimization of EtNBS-PDT Against Hypoxic Tumor Environments with a Tiered, High-Content, 3D Model Optical Screening Platform", Molecular Pharmaceutics, 9(11), Sep. 4, 2012, ISSN: 1543-8384, pp. 3171-3182, Published in final edited form as Molecular Pharmaceutics, Nov. 5, 2012, 9(11), pp. 3171-3182.

(Continued)

*Primary Examiner* — Michael G. Hartley
*Assistant Examiner* — Melissa J Perreira
(74) *Attorney, Agent, or Firm* — Novick, Kim & Lee, PLLC; Allen Xue

(57) ABSTRACT

A photosensitizer and derivative, application thereof. The photosensitizer has the structure of general formula I, wherein X is S or Se, Y is organic or inorganic ion, $R_1$ and $R_2$ are independently selected from H, alkyl, alkoxy, alkyl amido, alkyl azide and the like; $R_3$ is selected from H, alkyl, alkoxy, amino sulfonyl, hydroxyl, carboxyl and the like, and $L_1$ is a linker selected from —$(CH_2)_{n1}$— or —$(CH_2CH_2O)_{n2}$—. The derivatives are molecular medicines with drug molecules of anticancer and chemotherapy or tumor targeting function connected to the said photosensitizer. The photosensitizer has excellent near infrared characteristics and low dark toxicity and is used in the field of photodynamic tumor therapy. The introduction of benzophenothiazine or benzophenoselenazine into derivatives with tumor-targeting function could improve the specific uptake of photosensitizer in tumor tissues. Moreover, clinical anticancer drugs can be introduced into the structure of benzophenothiazine or benzophenoselenazine to achieve the purpose of combining therapy of photodynamic therapy and chemotherapy.

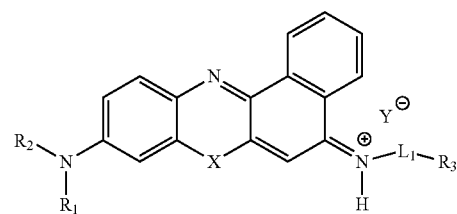

10 Claims, 7 Drawing Sheets

(51) Int. Cl.
   *A61B 10/00*        (2006.01)
   *A61K 41/00*        (2020.01)
   *A61K 47/55*            (2017.01)
   *A61K 31/405*           (2006.01)
   *C07D 421/12*           (2006.01)
   *A61P 35/00*            (2006.01)
   *C07D 417/12*           (2006.01)
   *C07D 293/10*           (2006.01)
   *C07D 279/18*           (2006.01)
   *A61K 31/4188*          (2006.01)
   *A61K 31/5415*          (2006.01)
   *C07D 279/36*           (2006.01)
   *A61K 31/55*            (2006.01)
   *C07D 495/04*           (2006.01)

(52) U.S. Cl.
   CPC .......... *A61K 31/5415* (2013.01); *A61K 31/55* (2013.01); *A61K 47/55* (2017.08); *A61K 47/551* (2017.08); *A61P 35/00* (2018.01); *C07D 279/18* (2013.01); *C07D 279/36* (2013.01); *C07D 293/10* (2013.01); *C07D 417/12* (2013.01); *C07D 421/12* (2013.01); *C07D 495/04* (2013.01)

(58) Field of Classification Search
   CPC .............. A61K 31/405; A61K 31/4188; C07D 279/36; C07D 293/10; C07D 417/12; C07D 421/12; C07D 495/04; C07D 279/18; A61P 35/00
   See application file for complete search history.

(56) References Cited

U.S. PATENT DOCUMENTS

2009/0192298 A1    7/2009  Burgess
2009/0259167 A1*  10/2009  Sakamoto ............ A61K 31/197
                                                       514/561
2016/0345834 A1*  12/2016  Hasan ................ A61B 1/00057

OTHER PUBLICATIONS

Daniela, V. et al.; "Structure-Function Relationships of Nile Blue (EtNBS) Derivatives as Antimicrobial Photosensitizers"; European Journal of Medicinal Chemistry, No. 75, Feb. 1, 2014 (Feb. 1, 2014), ISSN: 0223-5234, pp. 479-491.

* cited by examiner

PHOTOSENSITIZER AND DERIVATIVES AND APPLICATION THEREOF

TECHNICAL FIELD

The invention belongs to the field of anticancer drug design and synthesis, and specifically relates to the design, preparation and application of benzophenthiazine-like photosensitizer.

TECHNICAL BACKGROUND

According to the statistics of the world health organization (WHO), in the 1980s, about 7 million new cancer patients and 5 million people died of cancer every year in the world. Photodynamic therapy (PDT) is a method that applies the principles of photochemistry, photophysics and photobiology to the diagnosis and treatment of diseases. It has been known since ancient times that skin diseases could be treated with light, but it is not until the 19th century that it is accidentally discovered that ultraviolet light could work well for facial damage caused by tuberculosis. With the development of medical technology, people have also found that the method of light source irradiation has a good application in many aspects, such as killing microorganisms with ultraviolet light, treating and preventing diseases caused by vitamin D deficiency by shining sunlight or artificial light. In the past 30 years, with the rapid development of laser technology, molecular biology and optical signal technology transmitted by optical fiber, photodynamic therapy has attracted more and more attention and become an efficient and practical method for the treatment of malignant tumors and other diseases.

Photodynamic therapy has many different features to the surgery, radiotherapy and chemotherapy, such as noninvasive, repeated using without resistance, excellent selectivity, as well as low side effects on normal tissues at the same time. In the cases where radiotherapy or chemotherapy using for cancer treatments, photodynamic therapy can also be used to combine with these therapeutic modalities to achieve a certain synergistic effect. Therefore, photodynamic therapy provides a new method for the treatment of malignant tumors on the basis of conventional cancer treatments. With the progress of medical technology, this method has been widely used in the prevention and treatment of inner epithelial tumor, squamous cell carcinoma, actinic keratosis, brain tumor, esophageal cancer, skin cancer, lung cancer, prostate cancer, breast cancer, cervical cancer and other cancers, it has become one of the most active research fields in the world tumor prevention and treatment science.

Currently, porphyrin and phthalocyanine are the main representative of photosensitive agents applied in clinic. Although they have achieved great success in tumor treatment, there are still many defects, such as unstable composition ratio, slow metabolism, short maximum excitation wavelength, and photogenic toxic side effects, which seriously affect the actual effect of photodynamic therapy and its clinical transformation, therefore it is highly desired to design and develop ideal photosensitizers for enhancing the tumor therapeutic index while reducing side effects on healthy tissues.

As phenoxazine derivatives, benzophenothiazine and benzophenoselenazine compounds feature much advantages, for example high molar extinction coefficient and absorption wavelength in the near infrared region, good water solubility, low dark cytotoxicity, ideal cell membrane penetration, and so on. Since their appearance, they have attracted extensive attention in the field of functional materials. In addition, these derivatives have ideal pharmacological activities and have been widely used in anti-malaria, depression, dopamine and Parkinson's disease. However, in the field of photodynamic tumor therapy, there are relatively few studies on this kind of photosensitizer. In addition, it is of great practical significance for the development and clinical use of new photosensitizer to connect molecular targeted drugs or clinical chemotherapy drugs with photosensitizer molecules and build an integrated photosensitizer system with targeted cancer therapy and image-mediated diagnosis and treatment.

Content of Invention

The purpose of the present invention is to provide a photosensitizer of benzophenothiazine and benzophenoselenazine with near infrared absorption photodynamic activity, and it's preparation method and application. This class of photosensitizer has high triplet state production rate and excellent maximum absorption/emission wavelength>660 nm. In addition, the photosensitizer synthesized by this invention has low dark toxicity and high phototoxicity, and is able to improve the specific intratumoral accumulation through functionalizing with tumor targeting molecules. On the other hand, clinical anticancer drugs can also be introduced into the structure of benzophenothiazine or benzophenoselenazine so as to achieve combination therapy of photodynamic therapy and chemotherapy, which enable to significantly maximizing the overall therapeutic effect while minimizing side effects.

The purpose of the invention is realized by the following technical scheme:

The present invention first discloses a photosensitizer of formula I:

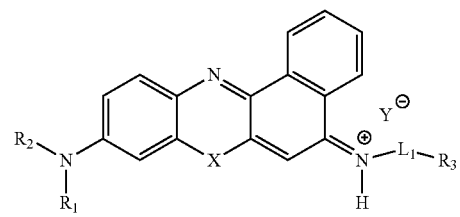

wherein:

X is S or Se;

Y is selected from the group consisting of halogen ion, $ClO_4^-$, $PF_6^-$, $BF_4^-$, $CH_3COO^-$ or $OTs^-$;

$R_1$ and $R_2$ are independently selected from the group consisting of H, alkyl, alkoxy, alkylamido, alkyl azide, alkylalkynyl, alkylamino, alkylsulfonyl, alkylhydroxy and alkylcarboxy;

$R_3$ is selected from the group consisting of H, alkyl, alkoxy, aryloxy, morpholinyl, carbonyl, amido, azido, alkynyl, amino, sulfonic acid, hydroxy and carboxy;

$L_1$ is a linking chain selected from $-(CH_2)_m-$ or $-(CH_2CH_2O)_n-$;

The m is an integer from 5 to 20, and the n is an integer from 2 to 20.

This current invention secondly discloses an application of the photosensitizer, which can be used to prepare antitumor drugs.

Thirdly, this current invention provides a derivative of the photosensitizer of Formula I, having the structure of general Formula II:

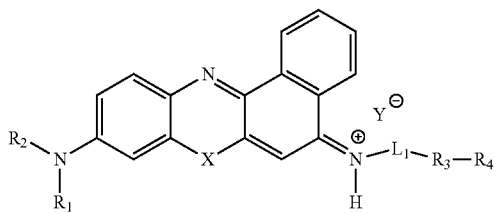

Wherein the $R_4$ is an anticancer and chemotherapy drug molecule or a molecular drug with tumor targeting function.

Fourthly, this current invention discloses application of the photosensitizer derivative, which can be used to prepare anti-tumor drugs.

The invention has the following advantages:

(1) the photosensitizer of the present invention has excellent near-infrared characteristics and has low bioluminescence bleach, light damage and biotoxicity when applied to biological imaging, and the generated fluorescence signal can penetrate deep biological tissue;

(2) The photosensitizer of the present invention can generate singlet oxygen under the light irradiation of a wavelength greater than 660 nm;

(3) The photosensitizer of the present invention has low dark toxicity, well biocompatibility, excellent water solubility, as well as ideal photostability, and can also be used as an excellent photosensitizers in the field of photodynamic tumor therapy.

(4) Mentioned in the present invention is put forward to the photosensitizers connecting with tumor targeting molecules or chemotherapy drug, which have the advantages of specific tumor targeting as well as improved intratumoral accumulation. Moreover, the clinical anticancer drugs also endow benzophenothiazine or benzophenoselenazine with enhanced therapeutic benefits, realizing combined therapy, that is synergistic photodynamic therapy and chemotherapy.

(5) The photosensitizer of the present invention has low untoward toxicities, single molecular structure, and good photostability. Importantly, such photosensitizers are easy to be prepared using readily available raw materials, which is conducive to the industrial production and preparation.

EMBODIMENTS

Figure 1:
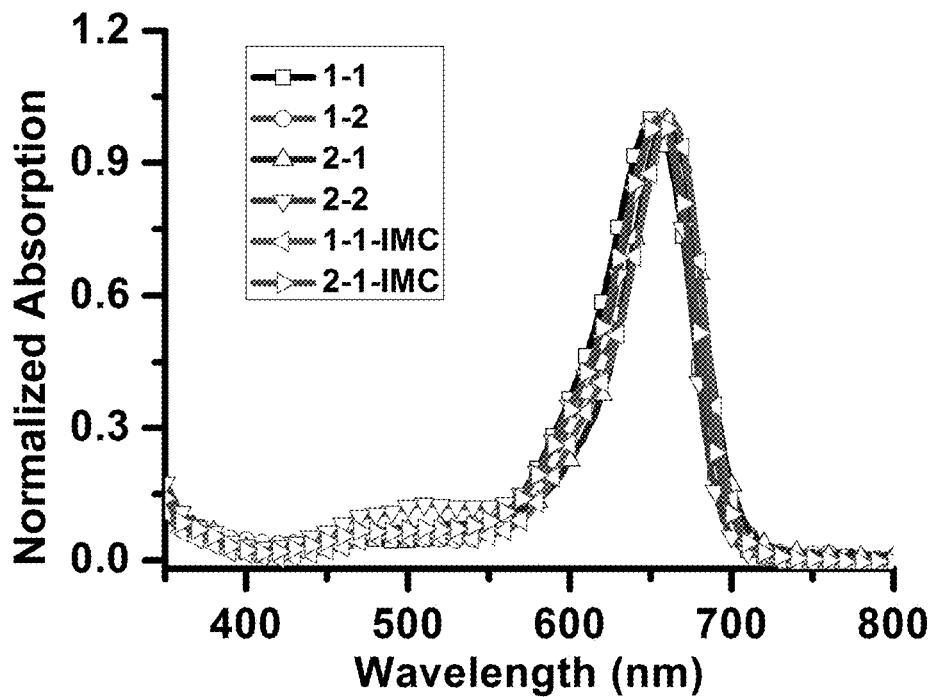
FIG. 1 is the normalized ultraviolet absorption spectrum of benzophenothiazine photosensitizer and benzophenoselenazine photosensitizer 1-1, 1-2, 2-1, 2-2, 1-1 IMC and 2-1 IMC in dichloromethane.

The method used to implement the invention is described in detail below, but the invention is not limited by it.

Firstly, this current invention disclose a photosensitizer of general formula I:

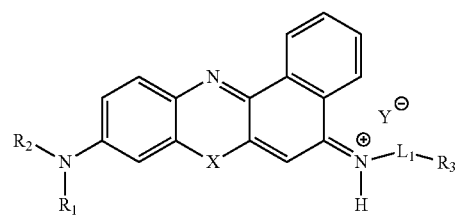

Wherein,

The said X is S or Se;

The said Y is selected from the group consisting of halogen ion, $ClO_4^-$, $PF_6^-$, $BF_4^-$, $CH_3COO^-$ or $OTs^-$;

$R_1$ and $R_2$ are independently selected from the group consisting of H, alkyl, alkoxy, alkylamido, alkyl azide, alkylalkynyl, alkylamino, alkylsulfonyl, alkylhydroxy and alkylcarboxy;

$R_3$ is selected from the group consisting of H, alkyl, alkoxy, aryloxy, morpholinyl, carbonyl, amido, azido, alkynyl, amino, sulfonic acid, hydroxy and carboxy;

$L_1$ is a linking chain selected from —$(CH_2)_m$— or —$(CH_2CH_2O)_n$—;

The m is an integer from 5 to 20, and the n is an integer from 2 to 20.

In the above photosensitizer, more specifically, the alkoxy groups includes but not limited to methoxyl, ethoxyl, n-butylated, tert-butylated, n-octylated and n-dodecaylated groups; The alkyl amide group includes but not limited to methyl carbonyl amino, ethyl carbonyl amino, dimethyl carbonyl amino, propyl carbonyl amino, amyl carbonyl amino, cyclohexyl carbonyl amino, 2-ethyl hexyl carbonyl amino, octyl carbonyl amino and dodecyl carbonyl amino. The alkyl azidine group includes but not limited to ethyl azidine, propyl azidine, butyl azidine and hexyl azidine; The alkyl amino group includes but not limited to ethyl amino group, dimethyl amino group, butyl amino group, cycloamyl amino group, 2-ethyl hexyl amino group and dodecyl amino group; The alkyl sulfonyl groups include but not limited to methyl sulfonyl groups, ethyl sulfonyl groups, butyl sulfonyl groups and cyclohexyl sulfonyl groups.

In the above photosensitizer, the halogens include fluorine, chlorine, bromine and iodine.

In the above photosensitizer, as a further optimization, $R_1$ and $R_2$ are independently selected from H, $C_{1-5}$ alkyl, $C_{1-5}$ alkoxy, $C_{2-5}$ alkyl alkyne, $C_{2-6}$ alkyl sulfonyl, $C_{2-6}$ alkyl azide. As a more specific embodiment, $R_1$ and $R_2$ are independently selected from H, methyl, ethyl, n-propyl, isopropyl, n-butyl, isobutyl, methoxy and ethoxy.

In the above photosensitizers, the $R_3$ is selected from amino, carboxyl, hydroxyl or azidine groups as a further preference.

In the above photosensitizer, the m or n is independently 5, 6, 7 or 8 as a further preference, In the above photosensitizer, the Y is a halogen ion as a further optimization.

In the above photosensitizer, as a more specific embodiment, the said photosensitizer is selected from:

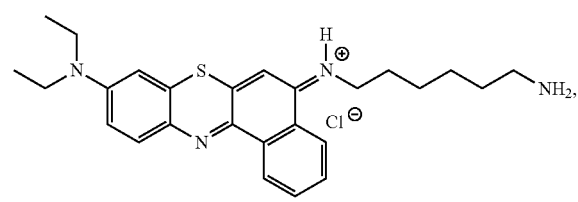

1-1

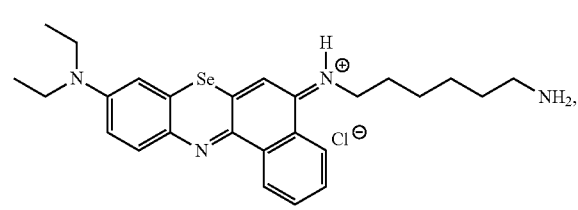

2-1

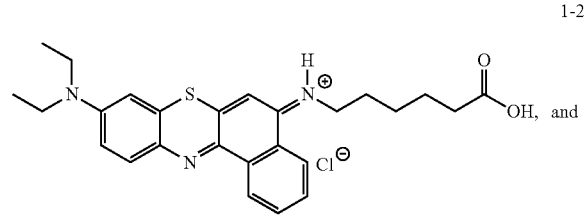

1-2

-continued

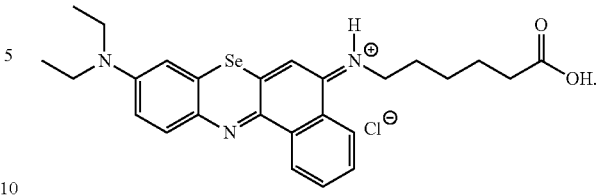

2-2

The invention also discloses a preparation method for the photosensitizer, including preparation of condensation intermediates containing sulfur or selenium with aniline derivatives as raw materials, preparation of naphthalene amine derivative intermediates, and synthesis steps of benzophenothiazine photosensitizers and benzophenoselenazine photosensitizers with the above two intermediates. Specifically, it includes the following steps:

Preparation of benzophenothiazine photosensitizer:

(1) In the ice bath condition, the p-phenylenediamine of corresponding $R_1$ and $R_2$ substituents is stirred in the aqueous solution in the presence of aluminum chloride, zinc chloride and sodium thiosulfate for 2-5 hours to prepare the corresponding monomer solid salt.

(2) Naphthalene derivatives is prepared by reflux reaction of 1-naphthalene or 1-bromonaphthalene and the corresponding compound $NH_2$-$L_1$-$R_3$ in the presence of alkaline catalyst for 2-24 hours;

(3) In the presence of potassium dichromate, the solid salt obtained in step (1) is then used to react with naphthalene amine derivatives in step (2) for 2-12 hours in methanol and dilute hydrochloric acid to prepare the corresponding benzophenthiazine photosensitizer.

Preparation of Benzophenoselenazine Photosensitizer:

The corresponding diselenium aniline monomer and naphthalene amine derivatives in step (2) react with CuO as catalyst and trifluoroethanol as solvent in the presence of dilute hydrochloric acid for 2-12 hours to prepare the corresponding benzophenoselenazine photosensitizer.

In the preparation method of benzothiazine photosensitizer, the $Al^{3+}$ solution in step (1) is aluminum chloride or aluminum sulfate.

In the mentioned preparation method of the benzophenothiazine photosensitizer, the reaction temperature in step (2) is 30-150° C. and the reaction time is 1-24 hours. The reaction solvent is dichloromethane, ethylene glycol monomethyl ether, methanol, DMF, ethanol, acetonitrile or their mixture. The molar ratio of 1-naphthalene or 1-bromonaphthalene to the corresponding compound with chain (-$L_1$-$R_3$) is 1:1-1:5. As a preferred embodiment, the reaction temperature is 90-140° C., the reaction time is 10-20 hours, and the molar ratio of 1-naphthaline or 1-bromonaphthalene to the corresponding compound with chain (-$L_1$-$R_3$) is 1:2-1:4.

In the mentioned preparation method of the benzophenthiazine photosensitizer, the compounds in step (3) or those in step (2) react with the compounds in step (1) in a molar ratio of 1:1-1:5 at a temperature of 20-120° C. and a reaction time of 4-12 hours with solvents selected from ethanol, DMF, DMSO, aqueous hydrochloride solution, methanol, dichloromethane or their mixture. As a preferred embodiment, the reaction temperature is 20-80° C., the reaction time is 2-8 hours, the reaction solvent is ethanol, methanol, DMF, hydrochloric acid aqueous solution or their mixture, and the compound in step (2) and the compound in step (1) are 1:1-1:4.

In the mentioned preparation method of benzoophenoselenazine photosensitizer, the molar ratio of naphthalene amine derivatives in step (2) and the corresponding diselenoaniline monomer is 1:1-1:5, the reaction temperature is 50-160° C., and the reaction time is 1-12 hours. The reaction solvent is selected from trifluoroethanol, aqueous solution of hydrochloric acid, methanol, dichloromethane or their mixture. As a preferred embodiment, the reaction temperature is 75-110° C., the reaction time is 2-8 hours, the reaction solvent is selected from trifluoroethanol, aqueous solution of hydrochloric acid, methanol or their mixture, and the molar ratio of naphthalene amine derivatives in step (2) to the corresponding diselenium aniline monomer is 1:1-1:4.

As a more specific embodiment, the present invention provides a preparation method for the photosensitizer compound 1-1, 1-2, 2-1, 2-2. The specific operation steps are as follows:

1) 1-bromonaphthalene react with 1, 6-hexane diamine to prepare compound I:

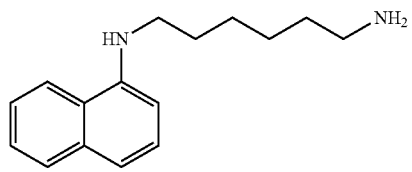

I

The reaction temperature is 80-150° C. and the reaction time is 1-24 hours. The reaction solvent is dichloromethane, ethylene glycol monomethyl ether, methanol, DMF or their mixture.

In the preferred embodiment, the reaction temperature is 90-140° C., the reaction time is 10-20 hours, the reaction solvent is selected from ethylene glycol monomethyl ether, methanol, DMF or their mixture, and the molar ratio of 1-bromonaphthalene to 1, 6-hexane diamine is 1:1-1:4.

In the further optimized embodiment, the reaction temperature is 100-130° C., the reaction time is 12-18 hours, the reaction solvent is selected from ethylene glycol monomethyl ether, DMF or their mixture, and the molar ratio of 1-bromonaphthalene to 1, 6-hexane diamine is 1:2-1:4.

In the most preferred embodiment, the reaction temperature is 110-125° C., the reaction time is 15-18 hours, the reaction solvent is ethylene glycol monomethyl ether, and the molar ratio of 1-bromonaphthalene to 1, 6-hexane diamine is 1:2-1:3.

2) 1-naphthylamine react with ethyl 6-bromohexanoate in a molar ratio of 1:1-1:5 to prepare the compound N-hexanoate ethyl ester 1-naphthylamine, followed by hydrolysis in sodium hydroxide solution and then acidification to prepare II:

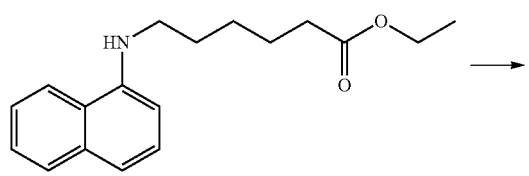

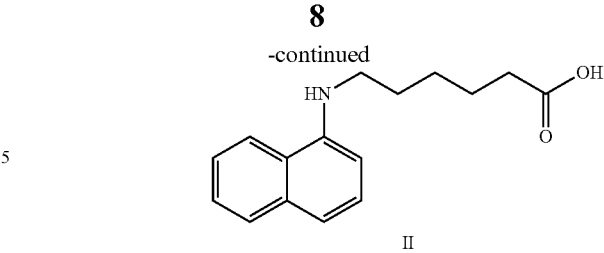

II

During the preparation of the compound N-caproate ethyl ester group 1-naphthaline, the reaction temperature is 30-150° C. and the reaction time is 1-24 hours. The reaction solvent is dichloromethane, ethanol, acetonitrile, DMF and sodium hydroxide aqueous solutions.

In the preferred embodiment, the reaction temperature is 30-120° C., the reaction time is 1-12 hours, the reaction solvent is selected from ethanol, acetonitrile, DMF or their mixture, and the molar ratio of 1-naphthylamine to ethyl 6-bromohexanoate is 1:1-1:4.

In the further optimized embodiment, the reaction temperature is 60-120° C., the reaction time is 4-12 hours, the reaction solvent is selected from ethanol, DMF or their mixture, and the mole of 1-naphthylamine and ethyl 6-bromohexanoate is 1:1-1:3.

In the most preferred embodiment, the reaction temperature is 60-100° C., the reaction time is 8-12 hours, the reaction solvent is ethanol, and the mole of 1-naphthylamine and ethyl 6-bromohexanoate is 1:1-1:2.

3) compound I or II react with the compound in formula i respectively in accordance with the molar ratio of 1:1-1:5 to prepare compounds 1-1 and 1-2:

The reaction temperature is 20-120° C. and the reaction time is 4-12 hours. The reaction solvent is ethanol, DMF, DMSO, aqueous hydrochloride solution, methanol, dichloromethane or their mixture.

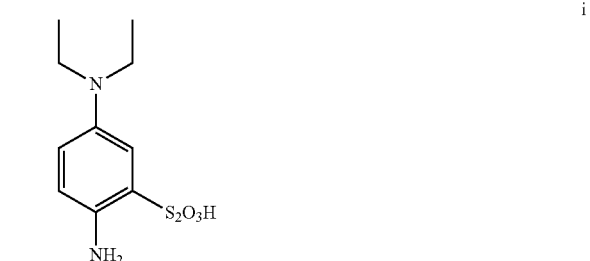

i

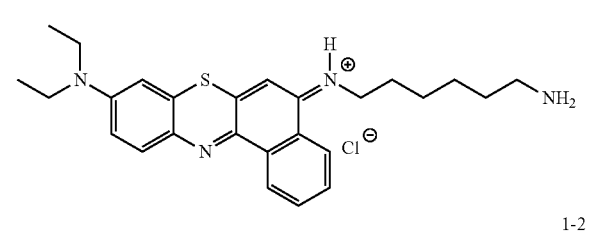

1-1

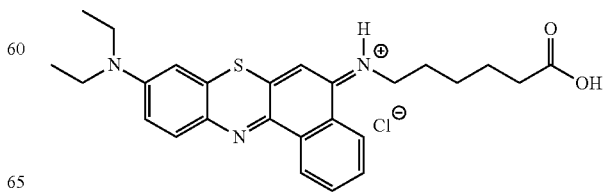

1-2

In the preferred embodiment, the reaction temperature is 20-80° C., the reaction time is 2-8 hours, the reaction solvent is ethanol, methanol, DMF, hydrochloric acid aqueous solution or their mixture, and the molar ratio of compound I or II to formula i is 1:1-1:4.

In the further optimized embodiment, the reaction temperature is 20-60° C., the reaction time is 2-6 hours, the reaction solvent is methanol, hydrochloric acid aqueous solution or their mixture, and the molar ratio of compound I or II to formula i is 1:1-1:3.

In the optimal embodiment, the reaction temperature is 20-50° C., the reaction time is 2-3 hours, the reaction solvent is a mixture of methanol and hydrochloric acid aqueous solution, and the molar ratio of compound I or II to formula i is 1:1-1:2

4) compound I or II reacts with the compound of formula ii to prepare compound 2-1 and 2-2 according to the molar ratio of 1:1-1:5:

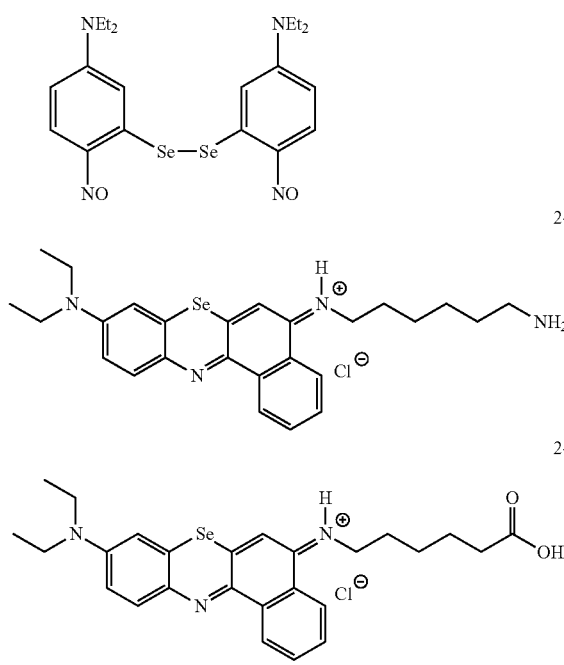

The reaction temperature is 50-160° C. and the reaction time is 1-12 hours. The reaction solvent is trifluoroethanol, aqueous solution of hydrochloric acid, methanol, dichloromethane or their mixture.

In the preferred embodiment, the reaction temperature is 75-110° C., the reaction time is 2-8 hours, the reaction solvent is trifluoroethanol, aqueous solution of hydrochloric acid, methanol or their mixture, and the molar ratio of compound I or II to formula ii is 1:1-1:4

In the further optimized embodiment, the reaction temperature is 80-100° C., the reaction time is 2-6 hours, the reaction solvent is trifluoroethanol, aqueous solution of hydrochloric acid or their mixture, and the molar ratio of compound I or II to formula ii is 1:1-1:3.

In the most preferred embodiment, the reaction temperature is 90-95° C., the reaction time is 2-3 hours, the reaction solvent is selected from the aqueous solution of trifluoroethanol, hydrochloric acid or a mixture of both, and the molar ratio of compound I or II to formula ii is 1:1-1:2.

The second technical purpose of the present invention is to provide an application of the photosensitizer, which can be used to prepare anti-tumor drugs.

The photosensitizer of the present invention has excellent near-infrared characteristics, low photobleaching, high phototoxicity, ideal fluorescence emitting that can penetrate deeply in biological tissues. Singlet oxygen can be generated under the irradiation of wavelength greater than 660 nm. Under the light irradiation using 660 nm light source, it can generate reactive oxygen species to kill tumor cells efficiently.

The third technical purpose of the present invention is to provide a class of derivatives of the photosensitizer, featuring the structure of general formula II:

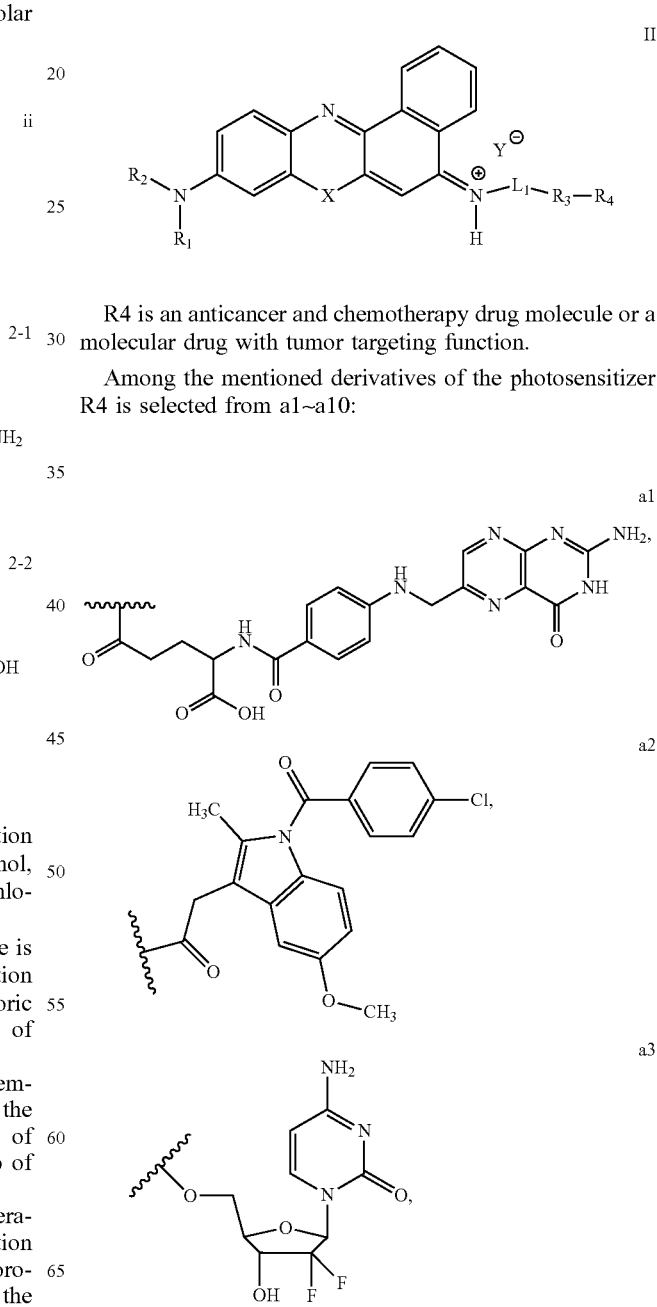

R4 is an anticancer and chemotherapy drug molecule or a molecular drug with tumor targeting function.

Among the mentioned derivatives of the photosensitizer R4 is selected from a1~a10:

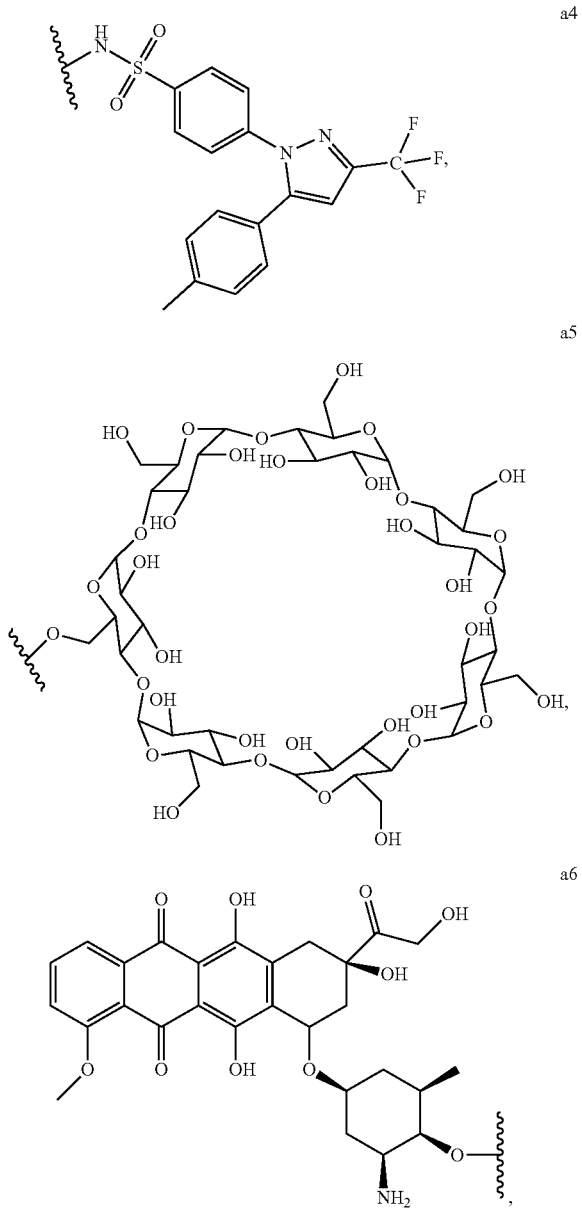
In the above cases, the curve represents the broken bond and positions where it is connected to the photosensitizer.
As a more specific embodiment, the derivatives are selected from the following compounds:
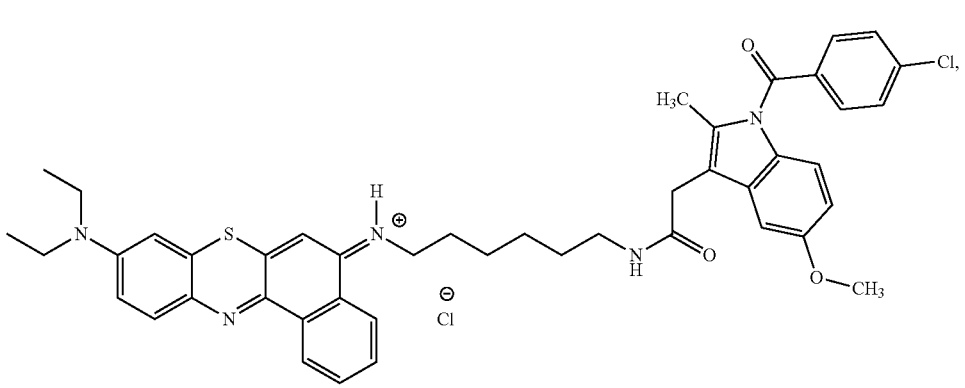

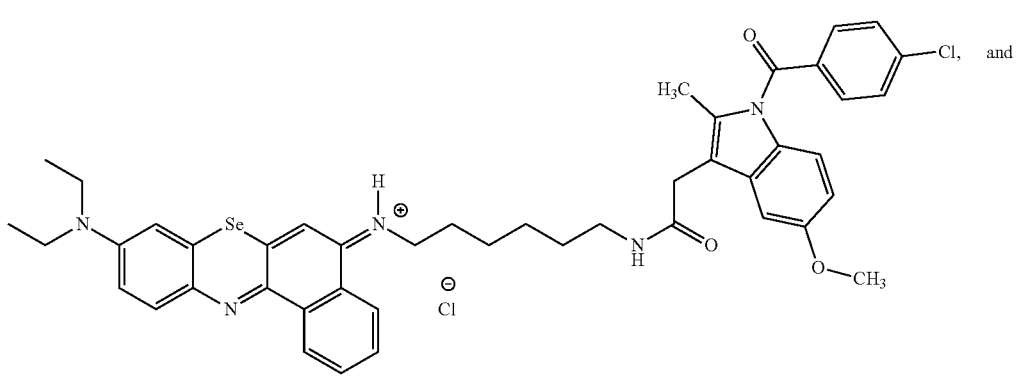

2-1-IMC and

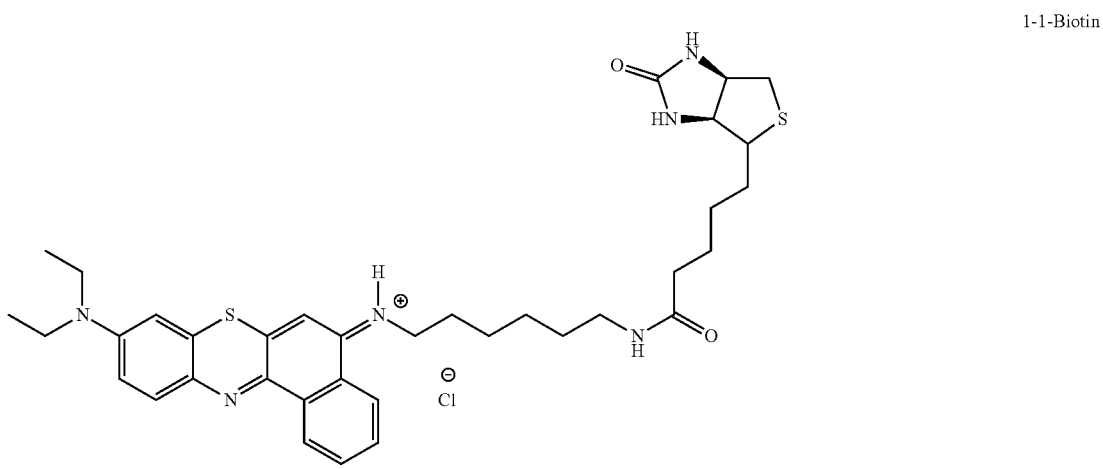

1-1-Biotin

The invention also discloses a preparation method for the photosensitizer derivative, including the reaction of the photosensitizer compound 1 with the corresponding molecular drug in molar ratio 1:1-1:3.

In the above preparation method, the reaction temperature is 0-100° C.; the reaction time is 12-48 hours; the reaction solvent is dichloromethane, ethanol, ethyl acetate, DMF or their mixture; the reaction is carried out in the presence of organic base with 4-dimethylaminopyridine as the catalyst. In the preferred embodiment, the reaction temperature is 10-80° C. and the reaction time is 12-32 hours. In the optimal embodiment, the reaction temperature is 25-40° C., the reaction time is 12-24 hours, and the reaction solvent is DMF.

As a more specific embodiment, the present invention provides a specific method for preparing compounds 1-1 IMC and 2-1 IMC:

Compounds 1-1 or 2-1 react with formula iii according to the molar ratio of 1:1-1:3 to prepare compounds 1-1 IMC and 2-1 IMC.

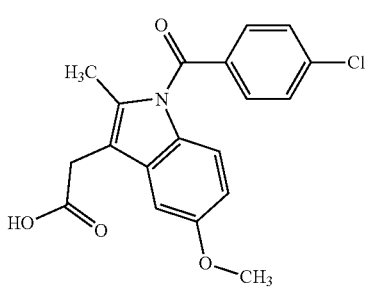

iii

-continued

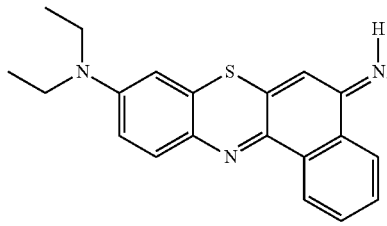
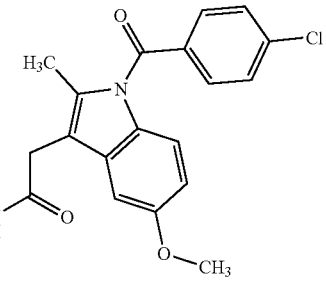

1-1IMC

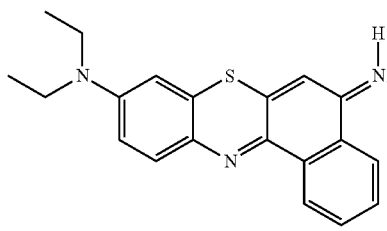
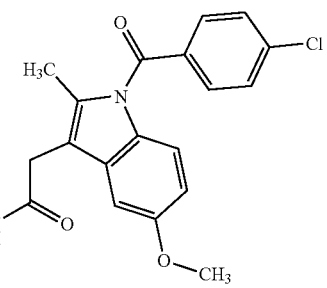

2-1-IMC

The reaction temperature is 0-100° C., the reaction time is 12-48 hours, the reaction solvent is dichloromethane, ethanol, ethyl acetate, DMF or their mixture, the reaction is carried out in the presence of organic base with 4-dimethylaminopyridine as the catalyst.

In the preferred embodiment, the reaction temperature is 10-80° C., the reaction time is 12-32 hours, the reaction solvent is dichloromethane, ethanol, DMF or its mixture, the reaction is carried out in the presence of organic base, with 4-dimethylaminopyridine as the catalyst, and the molar ratio of compound 1-1 or 2-1 to formula iii is 1:1-1:3.

In the further preferred embodiment, the reaction temperature is 20-70° C., the reaction time is 12-28 hours, the reaction solvent is dichloromethane, DMF or their mixture, the reaction is carried out in the presence of organic base, with 4-dimethylaminopyridine as the catalyst, and the molar ratio of compound 1-1 or 2-1 to formula iii is 1:1-1:2.

In the optimal embodiment, the reaction temperature is 25-40° C., the reaction time is 12-24 hours, the reaction solvent is DMF, the reaction is carried out in the presence of organic base, with 4-dimethylaminopyridine as the catalyst, and the molar ratio of compound 1-1 or 2-1 to formula iii is 1:1-1:1.5.

Benzophenothiazine photosensitizers and benzophenoselenazine photosensitizers and their derivatives synthesized by the above method are confirmed by nuclear magnetic resonance spectroscopy or mass spectrometry, and their structures are assisted by carbon spectroscopy.

The fourth technical purpose of the present invention is to provide applications of the photosensitizer derivatives, which can be used to prepare anti-tumor drugs.

The photosensitizer derivative of the invention has similar properties to the photosensitizer, and also has excellent near-infrared characteristics. When applied to biological imaging, it has low photobleaching, high phototoxicity, and ideal fluorescence emitting that can penetrate deeply in biological tissues. Singlet oxygen can be generated under the 660 nm light irradiation. Under the irradiation of laser wavelength greater than 660 nm, it has excellent photodynamic cell damage effects. After functioning with antitumor chemotherapy drugs or tumor targeting drug, the prepared photosensitizer derivative achieves tumor targeting ability or synergistic anticancer potency for improved cancer therapy.

The following non-restrictive embodiments may enable the general technical personnel in the field to understand the invention more fully without restricting it in any way.

Implementation Example 1

Synthesis of benzophene thiazine photosensitizer 1-1, 1-2:

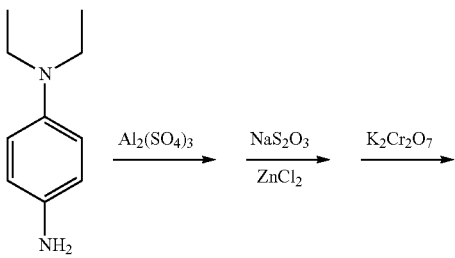

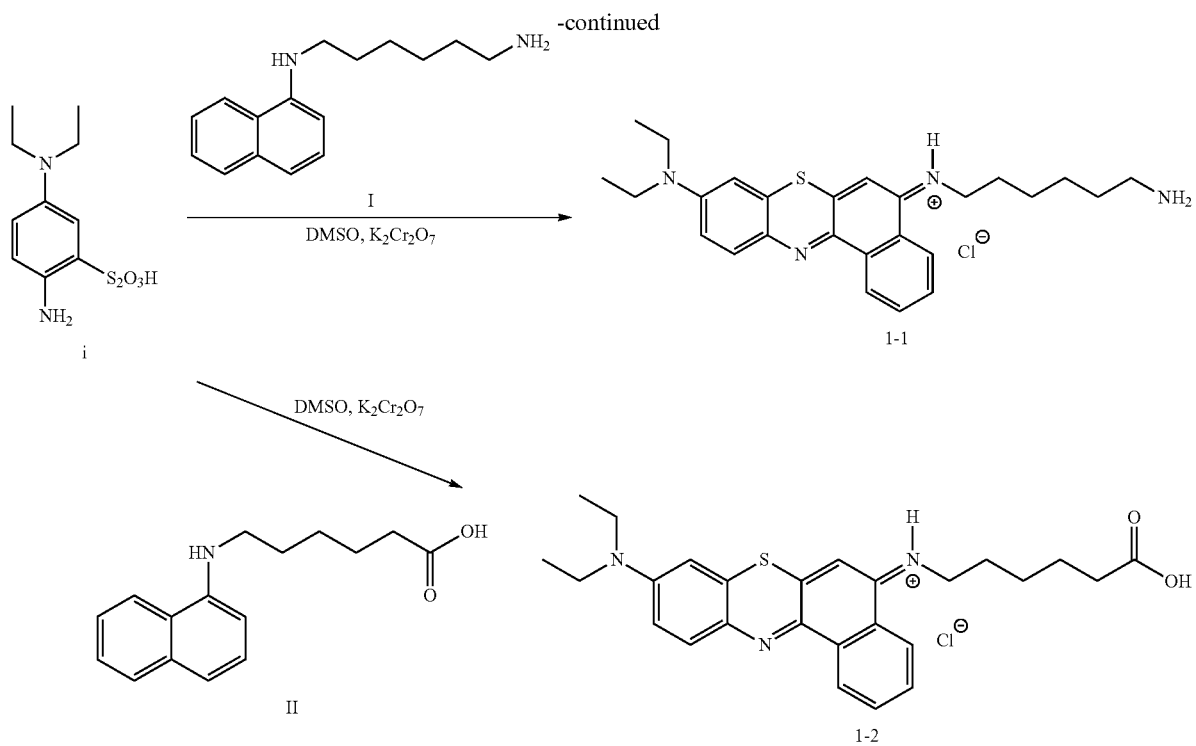

(1) Synthesis of Intermediate i

In 10 mL aqueous solution, 4-amino-N,N-diethyl aniline (6.09 g) and aluminum sulfate (4.11 g) are added. Then, the sodium thiosulfate (2.21 g) and zinc chloride (0.872 g) are added into the flask under ice bath. After that, 4 mL potassium dichromate aqueous solution (0.42 mmol) is slowly added and, continue to stir for 2 hours. After the reaction is finished, the crude produces are filtered, getting t a gray-black solid. Then, the filter cake is washed with acetone and ether, and then refluxed in 10 mL methanol for 20 minutes. 0.76 g light grey solid product is obtained after filtering, with a yield of 47%.

(2) Synthesis of Intermediate I 1-bromonaphthalene (4.12 g) and hexanediamine (4.65 g) are added to a round-bottomed flask containing 40 ml of egme solution. Then, CuI (190 mg) and $CsCO_3$ (3.0 g) are added, and the color of reaction solutions is changed from tan to blue-green. After reflux for 24 h, the crude produce is filtered and brown-yellow filtrate is purified by column chromatography, with a yield of 52%.

(3) Synthesis of Intermediate II 1-naphthylamine (1.6 g) and 6-ethyl bromohexanate (3.2 g) are dissolved in 6 mL ethanol in a 50 mL single-port bottle. After reflux reaction for 12 hours, ethanol is removed by vacuum distillation. Then 4 mL 1, 4-dioxane ring and 1.5 mL 1 M of sodium hydroxide are added and stirred for 5 hours, after the reaction is complete, adjusting the pH to about 3 with hydrochloric acid the intermediate II is separated by column chromatography with a yield of 55%.

(4-1) Synthesis of Benzophenothiazine 1-1

The light grey intermediates i (1.052 g) and intermediate I (1.5 g) are added to 20 mL dimethyl sulfoxide in room temperature, then 1.3 g potassium dichromate solid is added and stirred for ~20 min. When the solution turn brown, the resulted reaction solutions is transferred to 250 mL methanol, and 10 mL 2 mol·$L^{-1}$ hydrochloric acid is added dropwise. After stirring for 1 hour at room temperature, the water and methanol are removed by vacuum distillation. And then the remaining solution is slowly poured in 150 mL of saturated sodium chloride aqueous solution, the blue solid is precipitated, and the crude product is purified by silica gel column chromatography to obtain the blue solid product 1-1 with a yield of 30%. Nuclear magnetic: $^1H$ NMR (500 MHz, DMSO) δ 10.43 (s, 1H), 8.85 (d, J=49.0 Hz, 2H), 8.20 (s, 3H), 7.90 (s, 2H), 7.52 (s, 1H), 7.34 (s, 2H), 3.65 (s, 6H), 2.78 (s, 2H), 1.78 (s, 2H), 1.63 (s, 2H), 1.44 (s, 4H), 1.24 (s, 6H). $^{13}C$ NMR (126 MHz, DMSO) δ 153.04, 150.64, 139.70, 136.67, 133.75, 133.11, 131.83, 131.16, 129.49, 124.57, 123.96, 117.13, 105.36, 103.27, 45.07, 43.72, 39.89, 39.72, 39.56, 39.39, 39.22, 28.19, 26.76, 25.79, 25.46, 12.67.

(4-2) Synthesis of Benzophenothiazine 1-2

The light grey intermediates i (1.052 g) and intermediate II (1.7 g) are dissolved in 20 mL dimethyl sulfoxide in room temperature, then 1.4 g potassium dichromate solid is added and stirred for ~20 min. When the solution turn puce, the resulted reaction solutions is transferred to 250 mL methanol, and 10 mL 2 mol·$L^{-1}$ hydrochloric acid is added dropwise. After stirring for 1 hour at room temperature, the water and methanol are removed by vacuum distillation. And then the remaining solution is slowly poured in 150 mL of saturated sodium chloride aqueous solution, the blue solid is precipitated, and the crude product is purified by silica gel column chromatography to obtain the blue solid product 1-2 with a yield of 35%. Nuclear magnetic: $^1H$ NMR (500 MHz, DMSO) δ 12.01 (s, 1H), 10.15 (s, 1H), 8.95 (d, J=8.1 Hz, 1H), 8.66 (d, J=8.1 Hz, 1H), 8.03-7.88 (m, 2H), 7.84 (t, J=7.5 Hz, 1H), 7.53 (s, 1H), 7.37 (d, J=7.9 Hz, 2H), 3.67 (dt, J=21.1, 6.7 Hz, 6H), 2.25 (t, J=7.2 Hz, 2H), 1.82-1.72 (m, 2H), 1.65-1.54 (m, 2H), 1.44 (d, J=7.1 Hz, 2H), 1.23 (t, J=6.9 Hz, 6H). $^{13}C$ NMR (101 MHz, DMSO) δ 174.80, 153.41, 147.48, 139.36, 137.11, 133.83, 133.63, 132.21, 131.67, 131.57, 127.88, 125.01, 124.79, 124.41, 120.59, 109.04, 105.74, 46.75, 44.97, 34.01, 29.08, 28.54, 27.25, 13.07.

Determination of Properties of Compounds 1-1 and 1-2:

(1) Determination of UV absorption spectrum and fluorescence emission spectrum of benzophenothiazine photosensitizer 1-1, 1-2.

Figure 2:
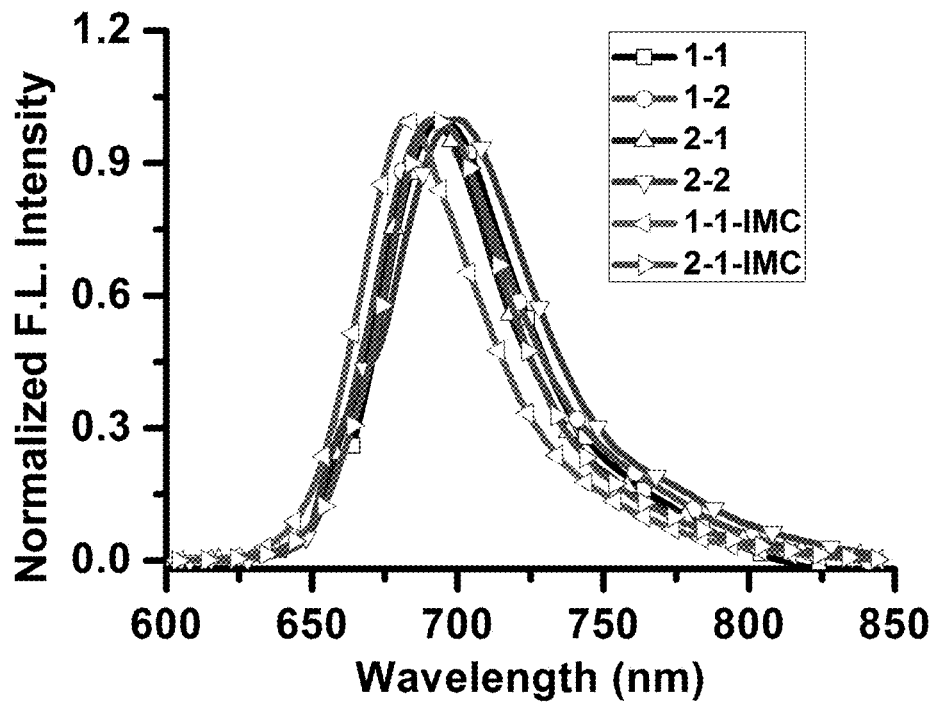
FIG. 2 is the normalized fluorescence emission spectrum of benzophenothiazine photosensitizer and benzophenoselenazine photosensitizer 1-1, 1-2, 2-1, 2-2, 1-1 IMC and 2-1 IMC in dichloromethane.

Compounds 1-1 and 1-2 synthesized from embodiment 1 above are added to 3 mL methanol solvent with a final concentration of 5 μM and their UV absorption spectra and fluorescence emission spectra are measured. The results display that the maximum absorption wavelength of benzophenothiazine photosensitizer 1-1 and 1-2 are 655 nm (as shown in FIG. 1), and the maximum emission wavelength is 694 nm (as shown in FIG. 2), localizing in the near infrared region, suggesting that both 1-1 and 1-2 can be used as near infrared photosensitizer. The instruments used are AgIllent 8453 UV spectrophotometer and AgIllent Cary EclIIpse fluorescence spectrophotometer.

(2) Determination of Singlet Oxygen Production of Benzophenothiazine Photosensitizer 1-1, 1-2

Compounds 1-1 and 1-2 synthesized in the embodiment 1 are added to 3 mL methanol solvent with a final concentration of 5 μM. Next, 1, 3-diphenyl isobenzofuran (DPBF) is added, and adjusting the absorbance of DPBF in the solution to about 1.0. Then the ultraviolet absorption curve is measured. According to the changes of the absorbance value of DPBF at 411 nm after each irradiation (660 nm light source), the correlation curve between absorbance and time is drawn. With methylene blue (MB) as reference, the singlet oxygen yield is calculated using the following formula.

$$\Phi_{\Delta sam} = \Phi_{\Delta std}\left(\frac{m_{sam}}{m_{std}}\right)\left(\frac{F_{std}}{F_{sam}}\right)$$

Figure 3:
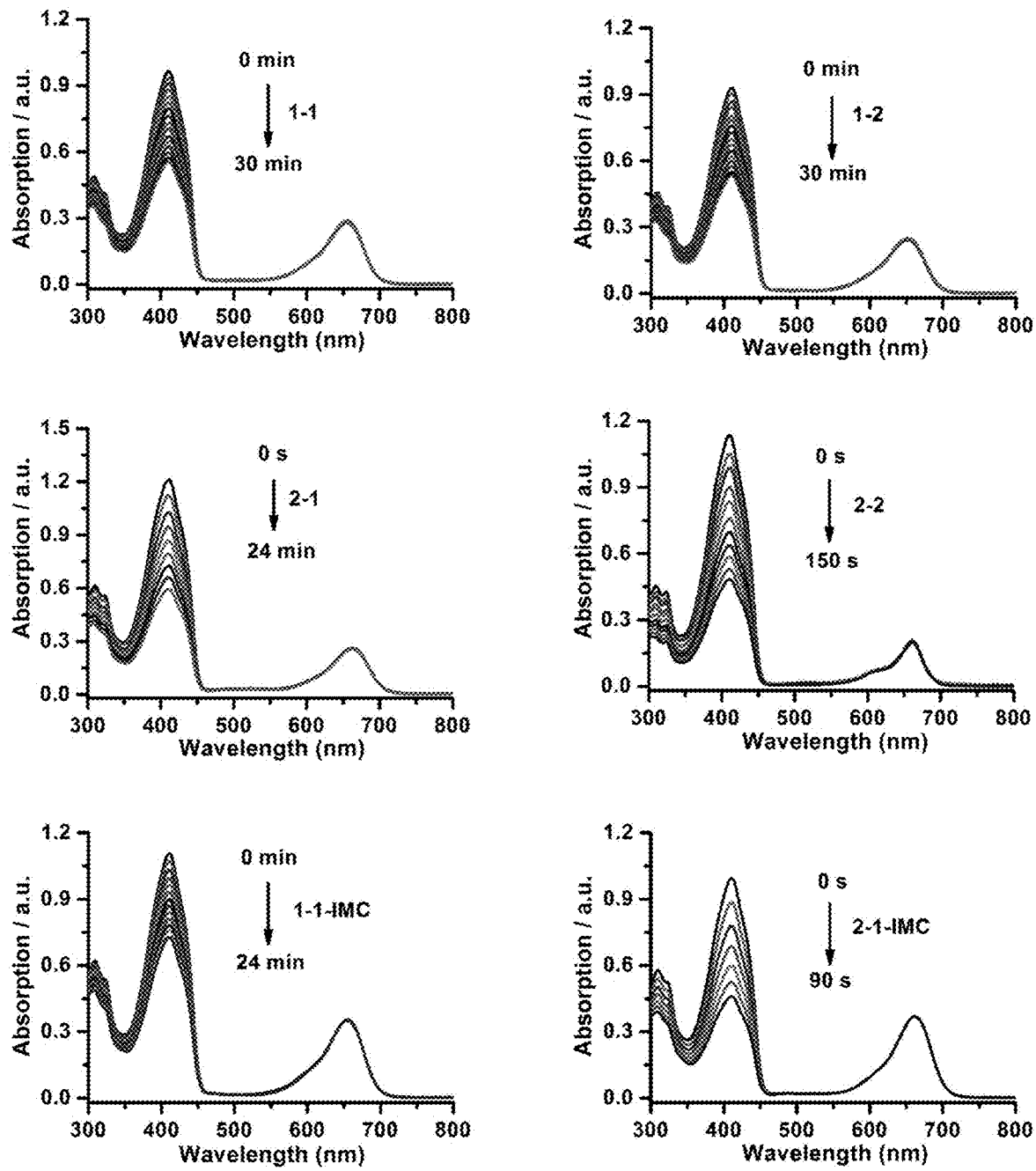
FIG. 3 is the DPBF absorption attenuation curve of benzophenothiazine photosensitizer and benzophenoselenazine photosensitizer 1-1, 1-2, 2-1, 2-1, 1-1 IMC and 2-1 IMC in the methanol system under the light irradiation of 660 nm light source.
Figure 4:
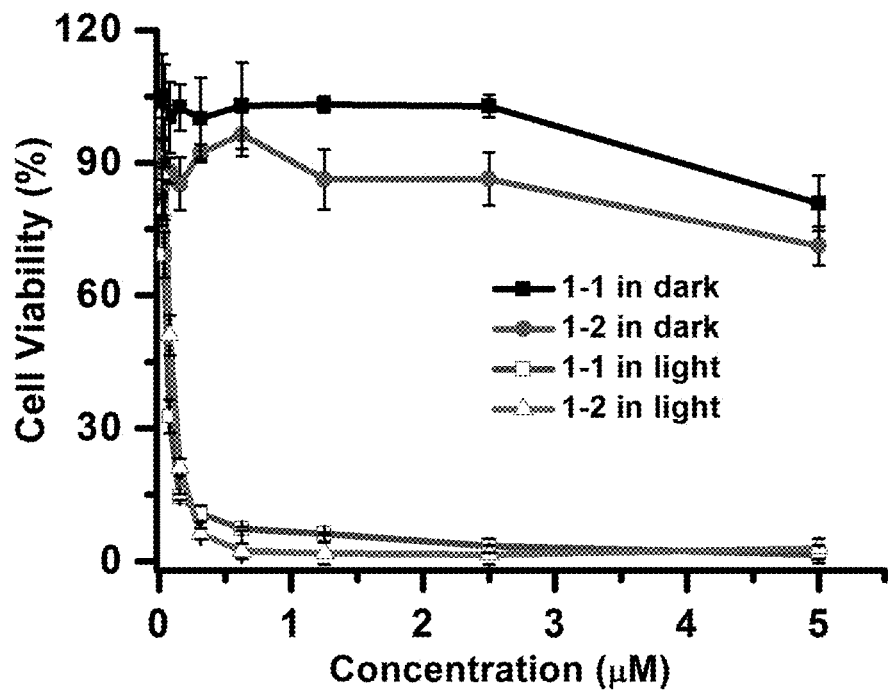
FIG. 4 is the anticancer results of benzophenothiazine photosensitizer 1-1 and 1-2 in vitro. MCF-7 is selected as the research object, and cell survival rate is used to characterize the cytotoxicity of photosensitizer. In dark means dark toxicity of photosensitizer. In light means phototoxicity.
Figure 5:
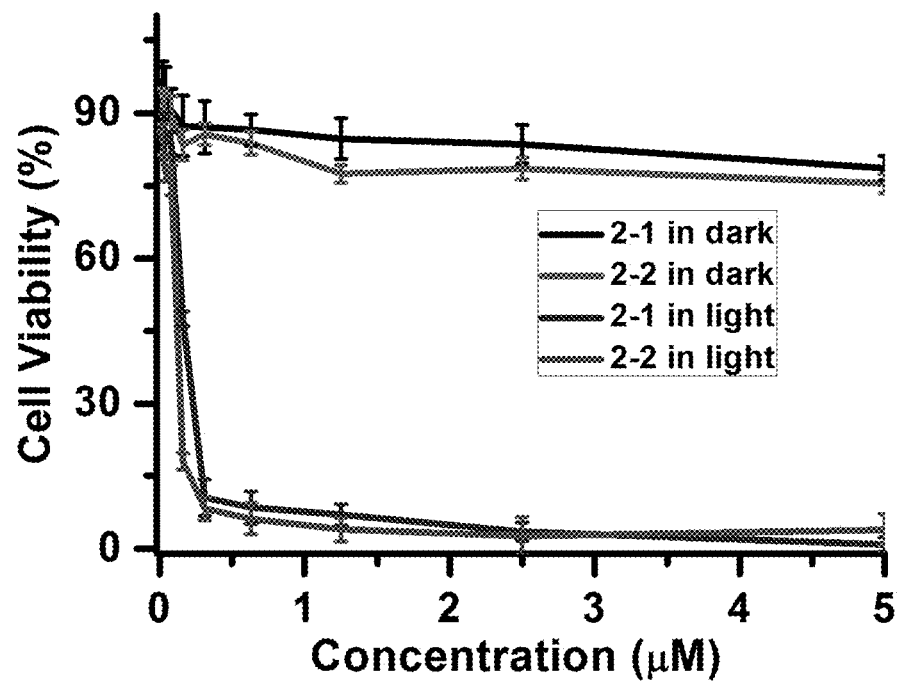
FIG. 5 is the anticancer results of benzophenoselenazine photosensitizer 2-1 and 2-2 in vitro. MCF-7 is selected as the research object, and cell survival rate is used to characterize the cytotoxicity of photosensitizer. In dark indicates dark toxicity of photosensitizer. In light means phototoxicity.
Figure 6:
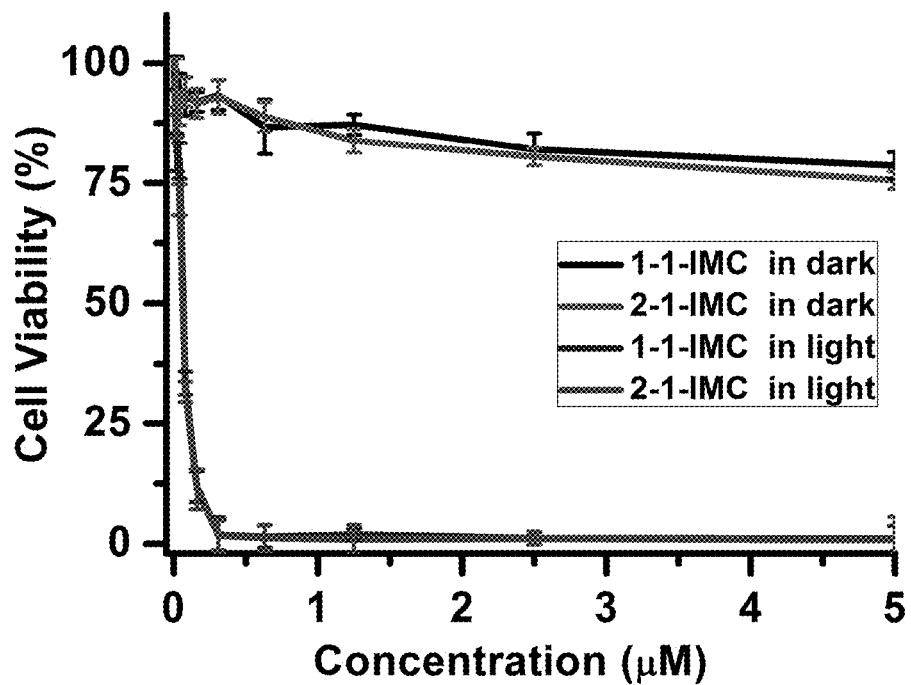
FIG. 6 is the anticancer results of the photosensitizer derivatives 1-1-IMC and 2-1-IMC in vitro. MCF-7 is selected as the research object, and cell survival rate is used to characterize the cytotoxicity of photosensitizer. In dark indicates dark toxicity of photosensitizer. In light means phototoxicity.

FIG. 3 shows the DPBF absorption attenuation curve of photosensitizer during the generation of singlet oxygen in methanol solution under the light condition of 660 nm. The results confirm that the singlet oxygen yield of 1-1 and 1-2 are both 0.04. The instruments used are AgIllent 8453 UV spectrophotometer, and the light source is 300 W xenon lamp.

(3) Anticancer Tests of Benzophenothiazine Photosensitizer 1-1 and 1-2 In Vitro Cell.

MCF-7 (human breast) cancer cells are incubated on the cell culture plate in DMEM medium supplemented with 10% FBS and 1% penicillin-streptomycin at 37° C. in a humidified, 5% $CO_2$ atmosphere. Then, the MCF-7 cells are seeded in 96 well cell culture plate at density of 5,000 cells per well. After 24 h incubation, 100 μL of 1-1 and 1-2 at different concentrations (5, 2.5, 1.25, 0.625, 0.32, 0.16, 0.08, 0.04, 0.02 μM) are added into the each well, and cultured for 1 h. Then, the cell medium is replaced with 200 μL fresh medium. For the phototoxicity test, the 96-well plate is irradiated with 660 nm light source for 10 min and then cultured in the above environment for 12 hours. No light irradiation is used as control. Then 20 μL MTT solution with a concentration of 5 mg/mL is added into each well and incubated in the incubator for another 4 hours. The culture medium is then removed and 200 μL DMSO is added to each well, and the plate is gently shaken for 5 min at room temperature. Finally, the absorbance at 490 nm is measured with a Bio-Rad microplate reader and the cell viability is calculated by the following equation:

Cell Viability (%)=[Σ($Ai/\bar{A}$control×100)]/$n$

Ai is the absorbance of the ith group of data (I=1, 2 . . . , n), $\bar{A}$control is the average absorbance of the control hole of the drug, and the parallel experiment is more than 3 times.

Implementation Example 2

Synthesis of benzophenoselenazine photosensitizer 2-1, 2-2:

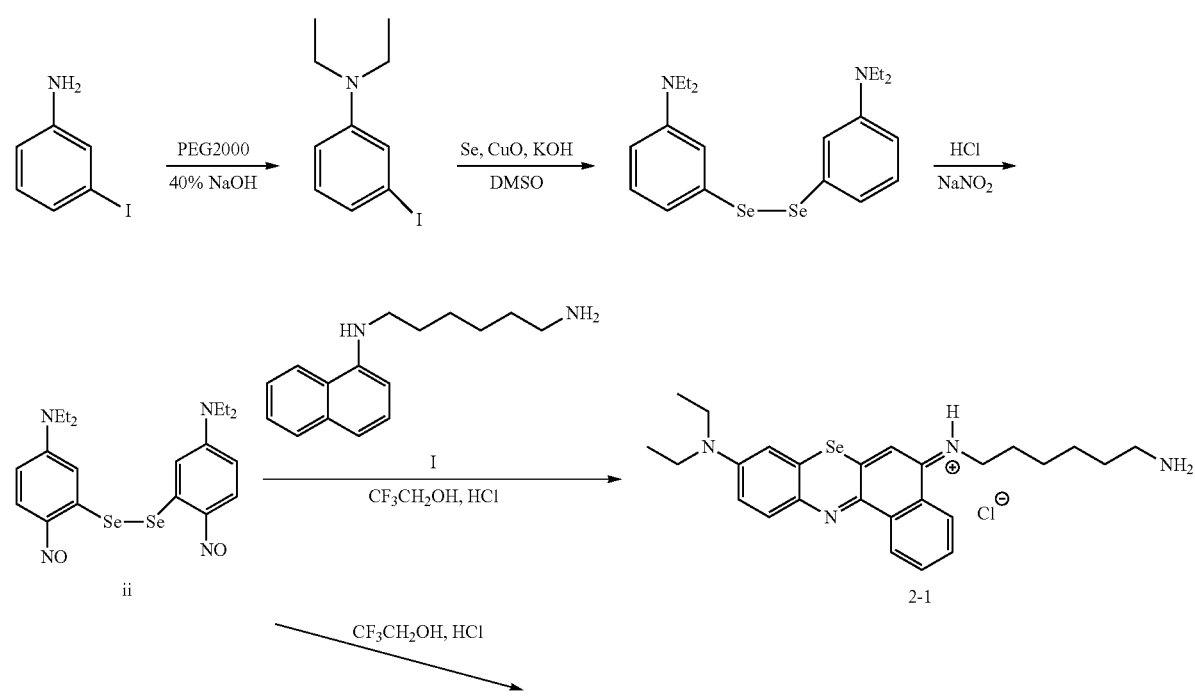

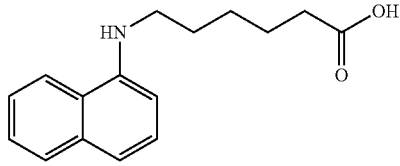

II

-continued

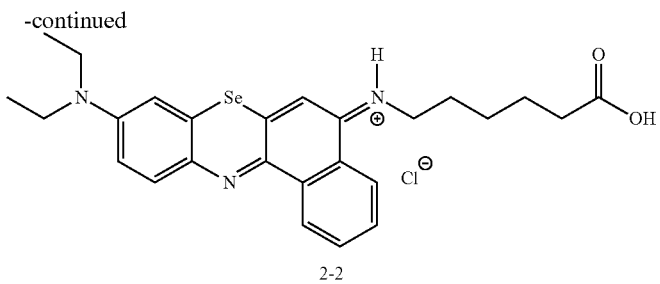

2-2

(1) Synthesis of Intermediate ii 0.7 g of 3-iodoaniline, 1.7 mL of iodoethane and 1.8 g of PEG2000 are added into 10 mL 40% of sodium hydroxide solution. After stirring at 45° C. for 12 hours, the reaction is cooled to room temperature and extracted with water and ether. The ether phase is collected. After removing the solvent, the crude product is purified by silica gel column chromatography, with yield of 55%.

Under nitrogen protection, g abovementioned 1 g produce, 0.8 g of copper oxide, 0.6 g of selenium powder, and 0.5 g of potassium hydroxide are dissolved in 15 mL dimethyl sulfoxide, and stirred overnight at 110° C. After the reaction is completed, the reaction solution is cooled to room temperature extracted with ethyl acetate and water. The ethyl acetate phase is collected and purified, giving red liquid products.

To 60 mL of hydrochloric acid containing the prepared light red liquid 1.2 g, 5 mL 6 mmol aqueous solution of sodium nitrite is added. During the reaction, the color of reaction solution turn from yellow to orange slowly, and produce a large number of solid. After stirring for 10 min, the solid products are filtrated and the filtrate is extracted by methylene chloride. With isopropyl alcohol recrystallization, the crude product is obtained as orange solid, with the yield of 70%.

(2-1) Synthesis of Benzophenoselenazine 2-1

After adding 0.315 g intermediate I and 0.25 g intermediate ii into 5 mL trifluoroethanol, 4 mL hydrochloric acid solution of 1 mol·$L^{-1}$ is then added and react at 90° C. for 2.5 hours. The reaction solvent is then removed under vacuum distillation, and crude product is washed by ethyl ether to remove the unreacted intermediate I. The remaining crude product is purified by silica gel column chromatography to obtain a blue solid with a yield of 45%. Nuclear magnetic $^1$H NMR (500 MHz, DMSO) δ 8.73 (s, 1H), 8.41 (d, J=7.2 Hz, 1H), 7.69 (d, J=21.7 Hz, 4H), 7.26 (s, 1H), 6.98 (s, 1H), 3.57 (d, J=45.7 Hz, 6H), 2.24 (t, J=7.3 Hz, 2H), 1.80-1.66 (m, 2H), 1.65-1.53 (m, 2H), 1.50-1.38 (m, 2H), 1.18 (dd, J=18.4, 11.5 Hz, 6H). $^{13}$C NMR (101 MHz, DMSO) δ 174.88, 158.72, 153.56, 151.24, 140.26, 137.26, 134.21, 133.69, 132.47, 131.72, 131.67, 130.03, 125.18, 124.74, 124.09, 123.54, 117.72, 105.85, 103.69, 45.57, 44.34, 34.08, 28.61, 26.46, 24.69, 13.14.

(2-2) Synthesis of Benzophenoselenazine 2-2

After adding 0.4 g intermediate II and 0.25 g intermediate ii into 5 mL trifluoroethanol, 4 mL hydrochloric acid solution of 1 mol·$L^{-1}$ is then added and react at 90° C. for 2.5 hours. The reaction solvent is then removed under vacuum distillation, and crude product is washed by ethyl ether to remove the unreacted intermediate II. The remaining crude product is purified by silica gel column chromatography to obtain a blue solid with a yield of 40%. Nuclear magnetic $^1$H NMR (500 MHz, DMSO) δ 8.73 (s, 1H), 8.41 (d, J=7.2 Hz, 1H), 7.69 (d, J=21.7 Hz, 4H), 7.26 (s, 1H), 6.98 (s, 1H), 3.57 (d, J=45.7 Hz, 6H), 2.24 (t, J=7.3 Hz, 2H), 1.80-1.66 (m, 2H), 1.65-1.53 (m, 2H), 1.50-1.38 (m, 2H), 1.18 (dd, J=18.4, 11.5 Hz, 6H). $^{13}$C NMR (101 MHz, DMSO) δ 174.88, 158.72, 153.56, 151.24, 140.26, 137.26, 134.21, 133.69, 132.47, 131.72, 131.67, 130.03, 125.18, 124.74, 124.09, 123.54, 117.72, 105.85, 103.69, 45.57, 44.34, 34.08, 28.61, 26.46, 24.69, 13.14.

Determination of Properties of Benzophenoselenazine Photosensitizer 1-1 and 1-2:

(1) Determination of UV Absorption Spectrum and Fluorescence Emission Spectrum of Benzophenoselenazine Photosensitizer 2-1, 2-2.

Benzophenoselenazine photosensitizer 2-1, 2-2, synthesized from embodiment 2 above are added to 3 mL methanol solvent with a final concentration of 5 μM, and their UV absorption spectra and fluorescence emission spectra are measured. The results showed that the maximum absorption wavelength of benzophenoselenazine photosensitizer 2-1 and 2-2 is 661 nm (as shown in FIG. 1), and the maximum emission wavelength is 702 nm (as shown in FIG. 2), localizing within the near infrared region, suggesting that they can be used as near infrared photosensitizer. The instruments used are AgIIIent 8453 UV spectrophotometer and AgIIIent Cary EcIIIpse fluorescence spectrophotometer.

(2) Determination of Singlet Oxygen Production of Benzophenoselenazine Photosensitizer 2-1, 2-2

Compounds 1-1 and 1-2 synthesized in the above embodiment 2 are added to 3 mL methanol solvent with a final concentration of 5 μM. Then, the 1,3-diphenyl isobenzofuran (DPBF) is added, and the absorbance of DPBF in the solution is adjusted to about 1.0. Then the ultraviolet absorption curve is measured after each 660 nm red light irradiation. According to the changes of the absorbance value of DPBF at 411 nm, the correlation curve between absorbance and time is drawn. With methylene blue (MB) as reference, the following formula is used to calculate the oxygen yield of its singlet state.

$$\Phi_{\Delta sam} = \Phi_{\Delta std}\left(\frac{m_{sam}}{m_{std}}\right)\left(\frac{F_{std}}{F_{sam}}\right)$$

FIG. 3 shows that the DPBF absorption attenuation curve of photosensitizer during the generation of singlet oxygen in methanol solution under the light condition of 660 nm. The results show that the singlet oxygen yield of photosensitizer 2-1 and 2-2 are 0.78 and 0.73, respectively. The instruments used are AgIIIent 8453 UV spectrophotometer, and the light source is 300 W xenon lamp.

(3) Anticancer Tests of Benzophenoselenazine Photosensitizer 2-1 and 2-2 In Vitro Cell.

MCF-7 (human breast) cancer cells are incubated on the cell culture plate in DMEM medium supplemented with 10% FBS and 1% penicillin-streptomycin at 37° C. in a humidified, 5% $CO_2$ atmosphere. Then, the MCF-7 cells are seeded in 96 well cell culture plate at density of 5,000 cells per well. After 24 h incubation, 100 μL of 2-1 and 2-2 at different concentrations (5, 2.5, 1.25, 0.625, 0.32, 0.16, 0.08, 0.04, 0.02 μM) are added into the each well, and cultured for 1 h. Then, the cell medium is replaced with 200 μL fresh medium. For the phototoxicity test, the 96-well plate is irradiated with 660 nm light source for 10 min and then cultured in the above environment for 12 hours. No light irradiation is used as control. Then 20 μL MTT solution with a concentration of 5 mg/mL is added into each well and incubated in the incubator for another 4 hours. The culture medium is then removed and 200 μL DMSO is added to each well, and the plate is gently shaken for 5 min at room temperature. Finally, the absorbance at 490 nm is measured with a Bio-Rad microplate reader and the cell viability is calculated by the following equation:

Cell Viability (%)=[Σ($A_i$/$\bar{A}$control×100)]/$n$ $A_i$ is the absorbance of the ith group of data (I=1, 2 . . . , n), $\bar{A}$control is the average absorbance of the control hole of the drug, and the parallel experiment is more than 3 times.

Implementation Example 3

Synthesis of compound 1-1-IMC, 2-1-IMC, the derivatives of benzophenothiazine photosensitizers or benzophenoselenazine photosensitizers conjugated with COX-2 inhibitor indomethacin.

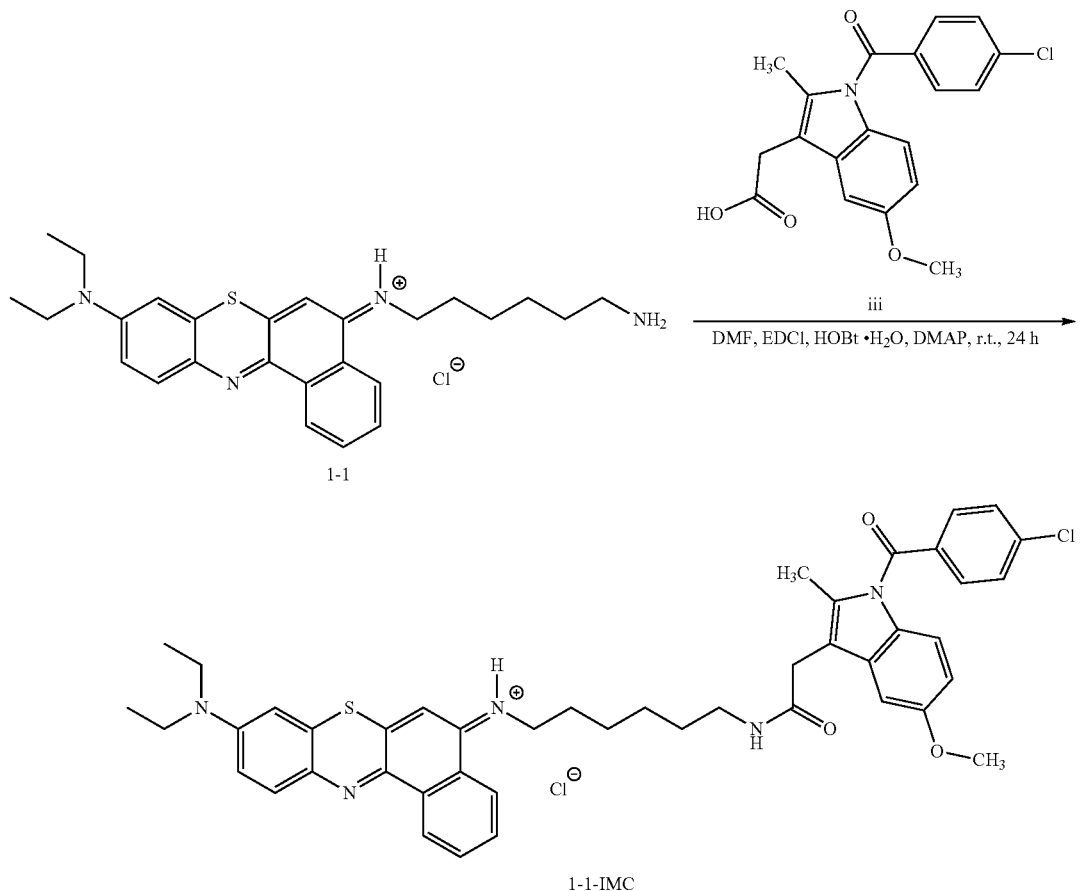

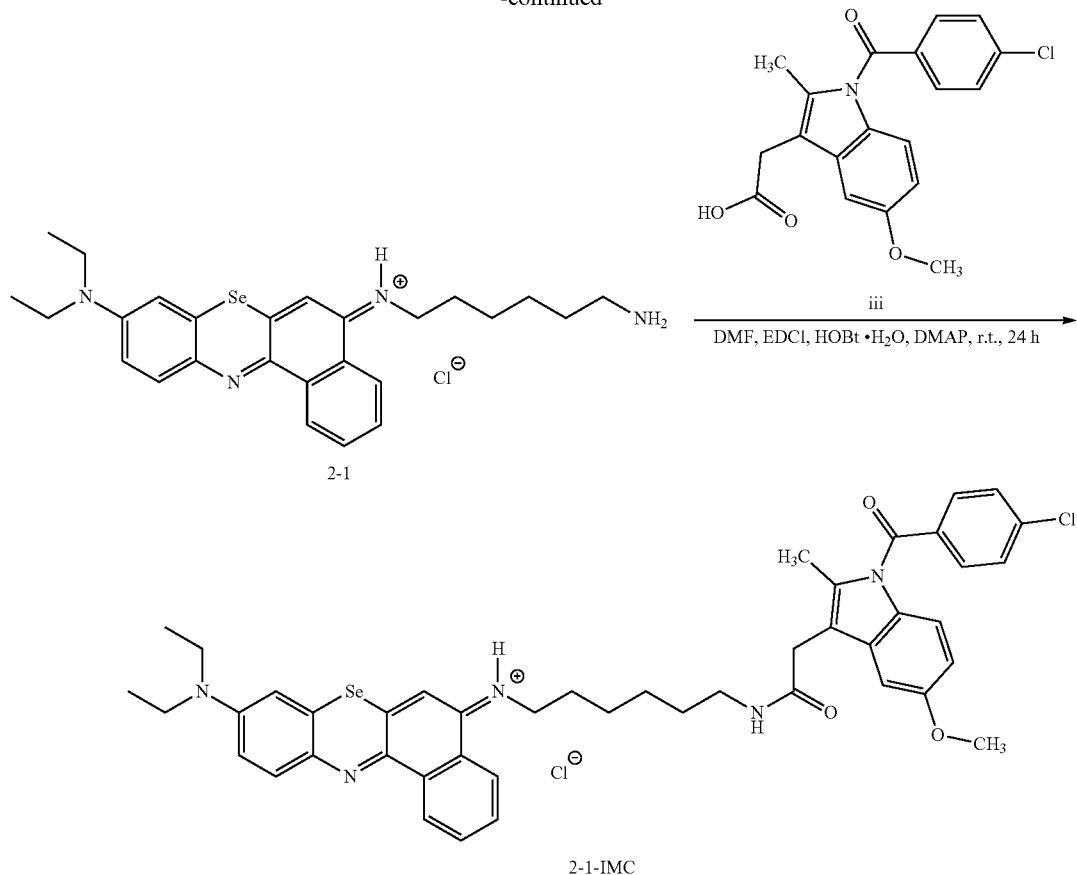

(1) Synthesis of 1-1-IMC, Derivatives of Benzophenothiazine Photosensitizer 1-1 Link with cox-2 Inhibitor-Indomethacin.

Benzophenothiazine 1-1 (120 mg), indomethacin (110.23 mg), 1-(3-dimethylaminopropyl)-3-ethyl carbon diimine (EDC) (70 mg), HOBt.H$_2$O (70 mg), and 4-methylpyridine (45 mg) are added into 10 mL DMF solution, and stirred for 24 hours at room temperature. After the reaction is finished, the solvent is evaporated under reduced pressure. A blue solid product is obtained by column chromatography with 66% yield.

Nuclear magnetic $^1$H NMR (500 MHz, CDCl$_3$) δ 10.94 (s, 1H), 9.02 (s, 1H), 8.92 (d, J=7.8 Hz, 1H), 7.92 (d, J=9.3 Hz, 1H), 7.73 (d, J=7.6 Hz, 2H), 7.61 (d, J=8.3 Hz, 2H), 7.41 (d, J=8.3 Hz, 2H), 7.34 (s, 1H), 7.09 (s, 2H), 6.95 (s, 1H), 6.85 (d, J=9.0 Hz, 2H), 6.58 (d, J=8.9 Hz, 1H), 3.79 (s, 3H), 3.71 (s, 4H), 3.59 (d, J=7.0 Hz, 4H), 3.25 (s, 2H), 2.35 (s, 3H), 1.81 (s, 2H), 1.50 (s, 2H), 1.42 (s, 4H), 1.33 (t, J=7.0 Hz, 7H). $^{13}$C NMR (126 MHz, CDCl$_3$) δ 170.83, 168.32, 156.12, 154.50, 150.41, 140.30, 139.02, 137.00, 135.96, 135.69, 134.08, 133.51, 132.10, 131.46, 131.14, 130.99, 130.89, 130.51, 130.22, 129.04, 128.69, 126.04, 125.15, 125.09, 125.01, 115.87, 114.89, 114.14, 111.92, 111.22, 104.50, 102.90, 101.49, 65.86, 55.87, 45.63, 43.86, 39.08, 32.08, 29.71, 28.79, 28.45, 27.18, 25.85, 25.65, 15.24, 14.15, 13.65, 12.75, 0.00.

(2) Synthesis of 2-1-IMC, Derivatives of Benzophenothiazine Photosensitizer 2-1 Link with cox-2 Inhibitor Indomethacin.

Add benzophenoselenazine 2-1 (126 mg), indomethacin (110.23 mg), 1-(3-dimethylaminopropyl)-3-ethyl carbon diimine (EDC) (70 mg), HOBt.H$_2$O (70 mg), and 4-methylpyridine (45 mg) are added into 10 mL DMF solution and stirred for 24 hours at room temperature. After the reaction is finished, the solvent is evaporated under reduced pressure. A deep blue solid product is obtained by column chromatography with 80% yield.

Nuclear magnetic $^1$H NMR (500 MHz, CDCl$_3$) δ 8.85 (d, J=8.1 Hz, 1H), 8.80 (s, 1H), 7.92 (d, J=9.3 Hz, 1H), 7.70 (d, J=7.6 Hz, 1H), 7.67-7.63 (m, 1H), 7.59 (d, J=8.3 Hz, 3H), 7.40 (d, J=8.4 Hz, 2H), 7.21 (dd, J=13.2, 6.7 Hz, 2H), 7.05 (s, 2H), 7.00 (d, J=9.3 Hz, 1H), 6.81 (d, J=9.0 Hz, 1H), 6.57 (dd, J=9.0, 2.2 Hz, 1H), 3.76 (s, 3H), 3.69 (s, 2H), 3.55 (d, J=7.0 Hz, 4H), 3.22 (s, 2H), 2.33 (s, 3H), 1.75 (s, 2H), 1.44 (d, J=16.5 Hz, 2H), 1.31 (t, J=7.0 Hz, 11H). $^{13}$C NMR (126 MHz, CDCl$_3$) δ 168.29, 156.10, 153.80, 150.14, 143.73, 139.05, 138.69, 135.99, 134.59, 134.53, 134.02, 132.21, 132.00, 131.12, 130.94, 130.87, 129.91, 129.04, 125.72, 125.42, 124.87, 124.60, 117.76, 115.47, 114.89, 114.02, 111.87, 111.07, 107.55, 106.82, 101.45, 55.82, 45.61, 44.08, 39.12, 32.05, 29.70, 28.83, 28.53, 25.86, 25.67, 13.59, 12.80, 0.00.

Determination of properties of Photosensitizer derivative 1-1-IMC, 2-1-IMC:

(1) Determination of UV Absorption Spectrum and Fluorescence Emission Spectrum of Photosensitizer Derivative 1-1-IMC, 2-1-IMC:

Compounds 1-1-IMC and 2-1-IMC synthesized from embodiment 3 above are added to 3 mL methanol solvent with a final concentration of 5 μM. The UV absorption spectra and fluorescence emission spectra are then measured. The results shows that the maximum absorption wavelength of benzophenothiazine photosensitizer 1-1-IMC and 2-1-IMC are 654 nm and 662 nm, respectively (as shown in FIG. 1), and the maximum emission wavelength are 694 nm and 703 nm, respectively (as shown in FIG. 2), localizing within the near infrared region, indicating they can be used as near infrared photosensitizer. The instruments used are AgIIlent 8453 UV spectrophotometer and AgIIlent Cary EcIIIpse fluorescence spectrophotometer.

(2) Determination of Singlet Oxygen Production of Photosensitizer Derivative 1-1-IMC. 2-1-IMC:

Compounds 1-1-IMC and 2-1-IMC synthesized in the above embodiment 2 are added to 3 mL methanol solvent with a final concentration of 5 μM. Then, the 1,3-diphenyl isobenzofuran (DPBF) is added, and the absorbance of DPBF in the solution is adjusted to about 1.0. Then the ultraviolet absorption curve is measured after each 660 nm red light irradiation. According to the changes of the absorbance value of DPBF at 411 nm, the correlation curve between absorbance and time is drawn. With methylene blue (MB) as reference, the following formula is used to calculate the oxygen yield of its singlet state.

$$\Phi_{\Delta sam} = \Phi_{\Delta std} \left( \frac{m_{sam}}{m_{std}} \right) \left( \frac{F_{std}}{F_{sam}} \right)$$

FIG. 3 shows the DPBF absorption attenuation curve of photosensitizer during the generation of singlet oxygen in methanol solution under the light condition of 660 nm. The results show that the singlet oxygen yield of photosensitizer derivative 1-1-IMC and 2-1-IMC are 0.04 and 0.82, respectively. The instruments used are AgIIlent 8453 UV spectrophotometer, and the light source is 300 W xenon lamp.

(3) Anticancer Tests of Photosensitizer Derivative 1-1-IMC and 2-1-IMC In Vitro Cell.

MCF-7 (human breast) cancer cells are incubated on the cell culture plate in DMEM medium supplemented with 10% FBS and 1% penicillin-streptomycin at 37° C. in a humidified, 5% $CO_2$ atmosphere. Then, the MCF-7 cells are seeded in 96 well cell culture plate at density of 5,000 cells per well. After 24 h incubation, 100 μL of 1-1-IMC and 2-1-IMC at different concentrations (5, 2.5, 1.25, 0.625, 0.32, 0.16, 0.08, 0.04, 0.02 μM) are added into the each well, and cultured for 1 h. Then, the cell medium is replaced with 200 μL fresh medium. For the phototoxicity test, the 96-well plate is irradiated with 660 nm light source for 10 min and then cultured in the above environment for 12 hours. No light irradiation is used as control. Then 20 μL MTT solution with a concentration of 5 mg/mL is added into each well and incubated in the incubator for another 4 hours. The culture medium is then removed and 200 μL DMSO is added to each well, and the plate is gently shaken for 5 min at room temperature. Finally, the absorbance at 490 nm is measured with a Bio-Rad microplate reader and the cell viability is calculated by the following equation:

Cell Viability (%)=[Σ($Ai/\overline{A}$control×100)]/$n$ $Ai$ is the absorbance of the ith group of data (I=1, 2 . . . , n), $\overline{A}$control is the average absorbance of the control hole of the drug, and the parallel experiment is more than 3 times.

Implementation Example 4

Synthesis of compound 1-1-Biotin, the derivatives of benzophenoselenazine photosensitizers link with Biotin.

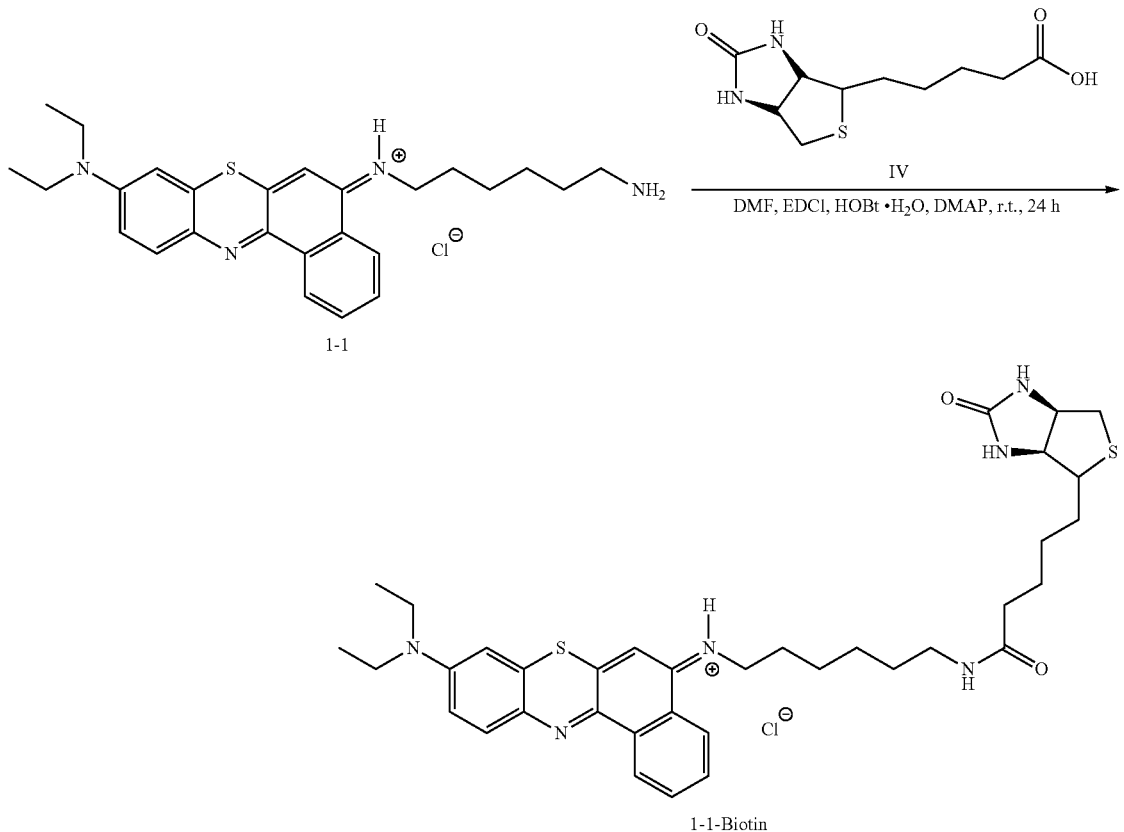

Synthesis of Benzothiazine Photosensitizer Targeting Derivatives 1-1-Biotin

Benzophenthiazine 1-1 (120 mg), biotin (125 mg), 1-(3-dimethylaminopropyl)-3-ethyl carbon diimine (EDC) (70 mg), HOBt.H$_2$O (70 mg), and 4-methylpyridine (45 mg) are added into 10 mL DMF solution and stirred for 24 hours at room temperature. After the reaction is finished, the solvent is evaporated under reduced pressure. The deep blue solid product is separated by column chromatography with a yield of 52%.

Nuclear magnetic $^1$H NMR (500 MHz, DMSO) δ 10.62 (s, 1H), 8.90 (d, J=8.1 Hz, 1H), 8.70 (d, J=8.0 Hz, 1H), 7.90 (dd, J=12.8, 7.4 Hz, 2H), 7.82 (dd, J=13.8, 6.2 Hz, 2H), 7.48 (s, 1H), 7.32 (s, 2H), 6.38 (d, J=23.4 Hz, 2H), 4.41-4.21 (m, 1H), 4.10 (s, 1H), 3.80-3.54 (m, 6H), 3.15 (s, 1H), 3.04 (d, J=5.6 Hz, 3H), 2.78 (dd, J=12.3, 4.9 Hz, 1H), 2.56 (d, J=12.4 Hz, 1H), 2.05 (t, J=7.2 Hz, 2H), 1.75 (d, J=6.5 Hz, 2H), 1.60 (d, J=4.4 Hz, 1H), 1.54-1.38 (m, 7H), 1.35 (d, J=5.6 Hz, 2H), 1.22 (d, J=7.0 Hz, 6H). $^{13}$C NMR (126 MHz, DMSO) δ 171.82, 162.66, 153.06, 150.63, 139.45, 136.60, 133.92, 133.13, 131.81, 131.12, 130.90, 129.49, 124.61, 123.75, 116.98, 106.90, 105.34, 103.37, 61.02, 59.17, 55.41, 45.03, 44.07, 40.03, 39.95, 39.86, 39.79, 39.69, 39.62, 39.52, 39.36, 39.19, 39.02, 38.22, 35.18, 29.07, 28.41, 28.17, 28.02, 26.10, 26.07, 25.32, 12.63.

Determination of the Properties of Derivative 1-1-Biotin (1) Determination of UV Absorption Spectrum and Fluorescence Emission Spectrum of Derivative 1-1-Biotin.

Figure 7:
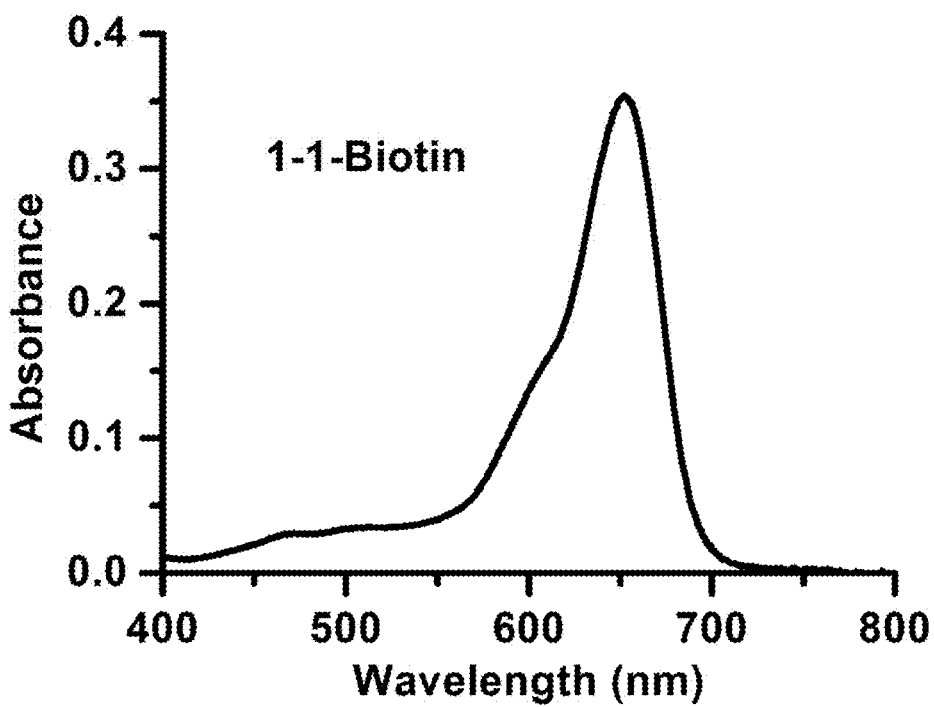
FIG. 7 is the ultraviolet absorption spectrum of the 1-1-biotin in dichloromethane which is the derivative of benzophenothiazine linked by Biotin.
Figure 8:
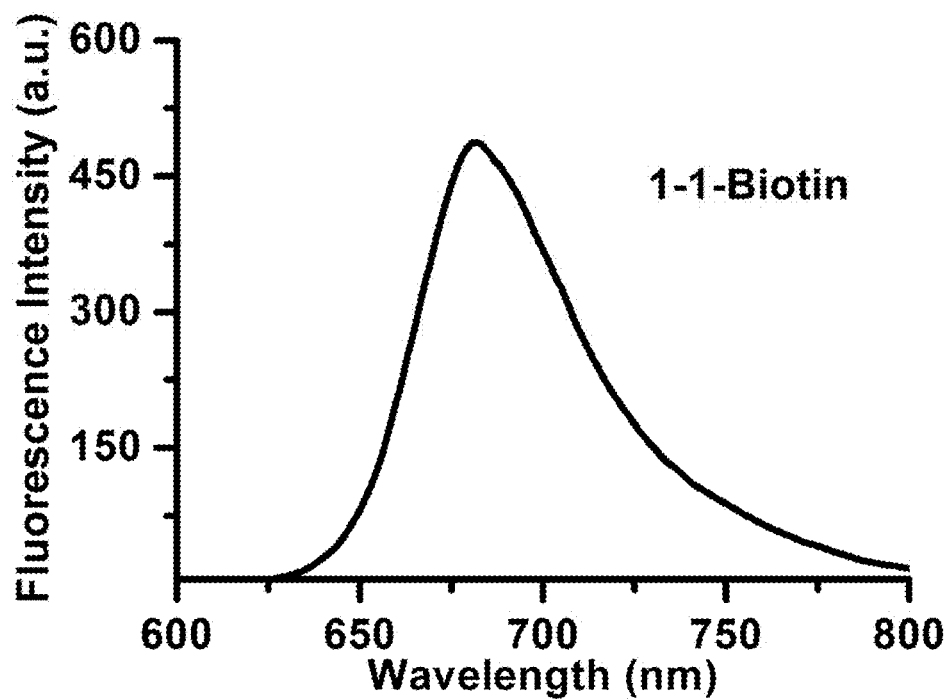
FIG. 8 is the fluorescence spectrum of the 1-1-biotin in dichloromethane which is the derivative of benzophenothiazine linked by Biotin.

Compounds 1-1-Biotin synthesized from embodiment 4 above is added to 3 mL methanol solvent with a final concentration of 5 μM, and then the UV absorption spectra and fluorescence emission spectra are detected. The results showed that the maximum absorption wavelength of 1-1-Biotin is 652 nm (as shown in FIG. 7), and the maximum emission wavelength is 681 nm (as shown in FIG. 8), localizing within the near infrared region, indicating they can be used as near infrared photosensitizer. The instruments used are AgIllent 8453 UV spectrophotometer and AgIllent Cary EclIIpse fluorescence spectrophotometer.

(2) Determination of Singlet Oxygen Production of Derivative 1-1-Biotin.

Compounds 1-1-Biotin synthesized in the above embodiment 2 are added to 3 mL methanol solvent with a final concentration of 5 μM. Then, the 1,3-diphenyl isobenzofuran (DPBF) is added, and the absorbance of DPBF in the solution is adjusted to about 1.0. Then the ultraviolet absorption curve is measured after each 660 nm red light irradiation. According to the changes of the absorbance value of DPBF at 411 nm, the correlation curve between absorbance and time is drawn. With methylene blue (MB) as reference, the following formula is used to calculate the oxygen yield of its singlet state.

$$\Phi_{\Delta sam} = \Phi_{\Delta std}\left(\frac{m_{sam}}{m_{std}}\right)\left(\frac{F_{std}}{F_{sam}}\right)$$

Figure 9:
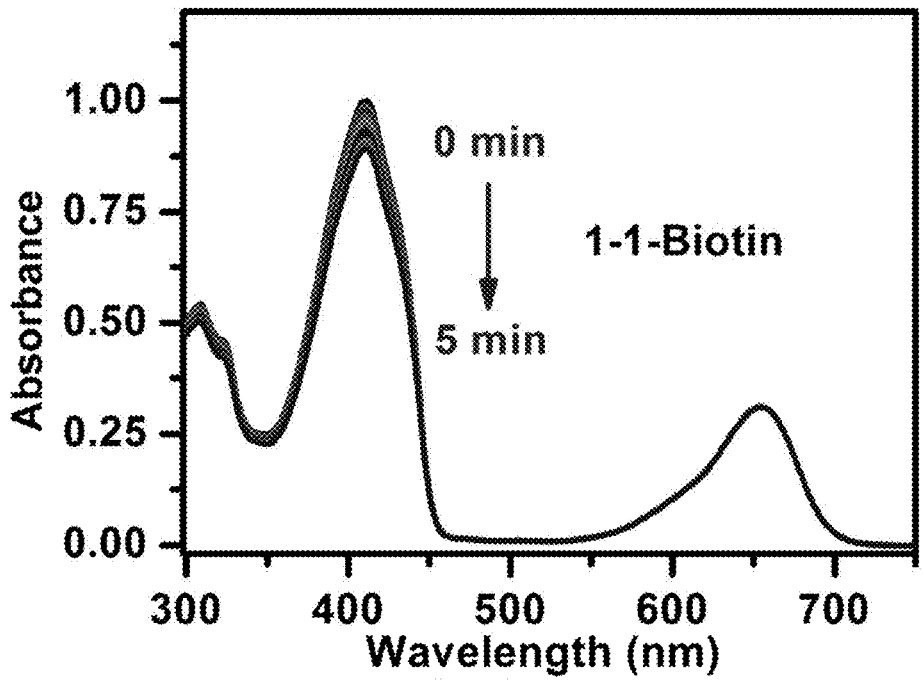
FIG. 9 is the DPBF absorption attenuation curve of the 1-1-biotin, which is the derivative of benzophenothiazine linked by Biotin, for the generation of singlet oxygen under 660 nm light irradiation in the dichloromethane system.

FIG. 9 shows the DPBF absorption attenuation curve of photosensitizer during the generation of singlet oxygen in methanol solution under the light condition of 660 nm. The results show that the singlet oxygen yield of 1-1-Biotin is 0.04. The instruments used are AgIllent 8453 UV spectrophotometer, and the light source is 300 W xenon lamp.

(4) Anticancer Tests of Derivative 1-1-Biotin In Vitro Cell.

MCF-7 (human breast) cancer cells or HepG2 (liver cancer cell) are incubated on the cell culture plate in DMEM medium supplemented with 10% FBS and 1% penicillin-streptomycin at 37° C. in a humidified, 5% CO$_2$ atmosphere. Then, the MCF-7 cells are seeded in 96 well cell culture plate at density of 5,000 cells per well. After 24 h incubation, 100 μL of 1-1-Biotin at different concentrations (5, 2.5, 1.25, 0.625, 0.32, 0.16, 0.08, 0.04, 0.02 μM) are added into the each well, and cultured for 1 h. Then, the cell medium is replaced with 200 μL fresh medium. For the phototoxicity test, the 96-well plate is irradiated with 660 nm light source for 10 min and then cultured in the above environment for 12 hours. No light irradiation is used as control. Then 20 μL MTT solution with a concentration of 5 mg/mL is added into each well and incubated in the incubator for another 4 hours. The culture medium is then removed and 200 μL DMSO is added to each well, and the plate is gently shaken for 5 min at room temperature. Finally, the absorbance at 490 nm is measured with a Bio-Rad microplate reader and the cell viability is calculated by the following equation:

Cell Viability (%)=[Σ($Ai/\overline{A}$control×100)]/$n$

Ai is the absorbance of the ith group of data (I=1, 2 . . . , n), $\overline{A}$control is the average absorbance of the control hole of the drug, and the parallel experiment is more than 3 times.

Figure 10:
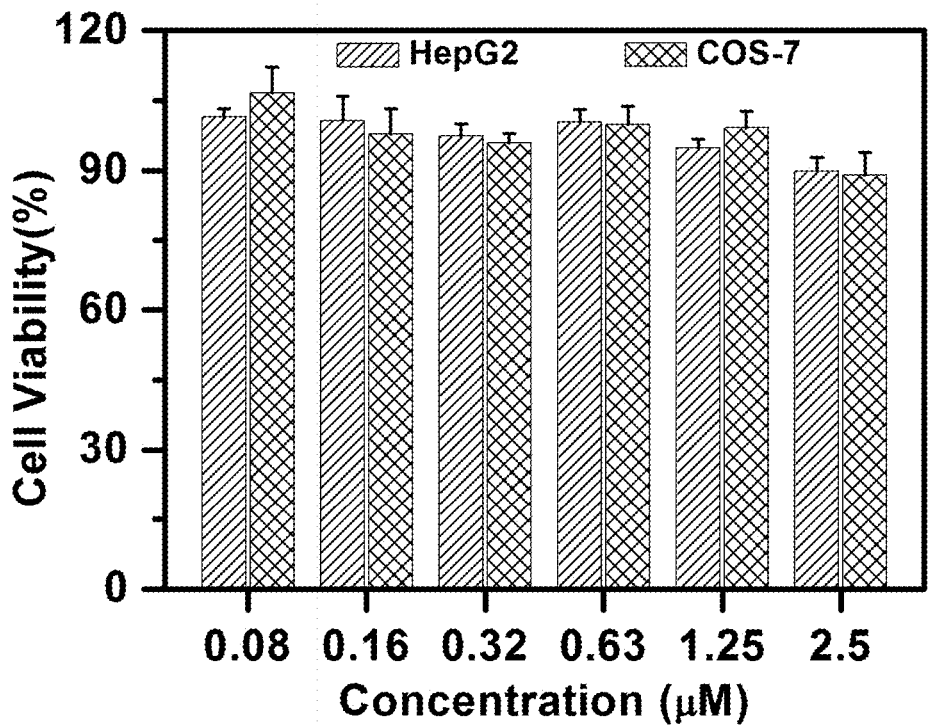
FIG. 10 is the dark toxicity results of the 1-1-biotin which is the derivative of benzophenothiazine linked by Biotin in vitro. HepG2 and COS-7 are selected as the study objects, and cell survival rate is used to characterize the cytotoxicity of photosensitizer.
Figure 11:
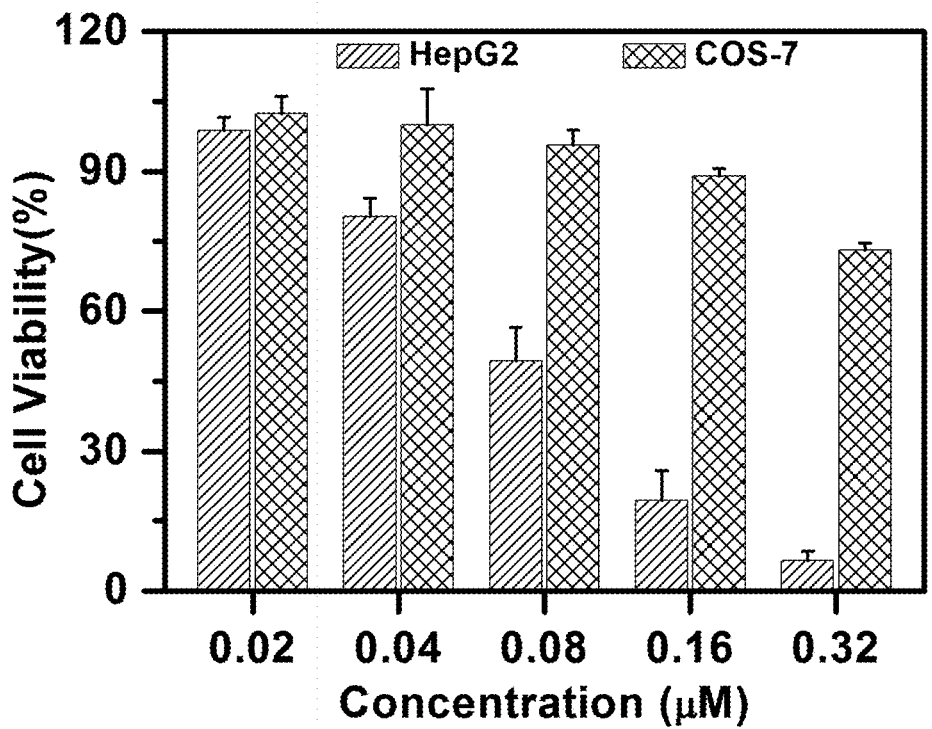
FIG. 11 shows the results of in vitro cytotoxicity test of the 1-1-biotin which is the derivative of benzophenothiazine linked by Biotin. HepG2 and COS-7 are selected as the study objects, and cell survival rate is used to characterize the cytotoxicity of photosensitizer.

As can be seen from FIG. 10, 1-1-Biotin has low dark toxicity to both HepG2 (hepatoma cells) and COS-7 (African green monkey kidney cells) cell lines. However, the phototoxicity in such two kind of cells are very different. After 10 minutes of irradiation with a 660 nm LED light source, significant HepG2 cells arr killed, while only limited cytotoxicity against COS-7 cells is noted (as shown in FIG. 11). The results demonstrate that the killing effect of 1-1-Biotin on biotin receptor overexpressing HepG2 cells is significantly higher than that on COS-7 cells with low biotin receptor expression. As such, the 1-1-Biotin, a derivative of benzophenothiazine and biotin, has achieved a certain selectivity for biotin overexpressing cells, and can exert the targeted photodynamic effects on typical tumors.

(5) Selectivity Test In Vitro Cell of 1-1-Biotin.

Figure 12:
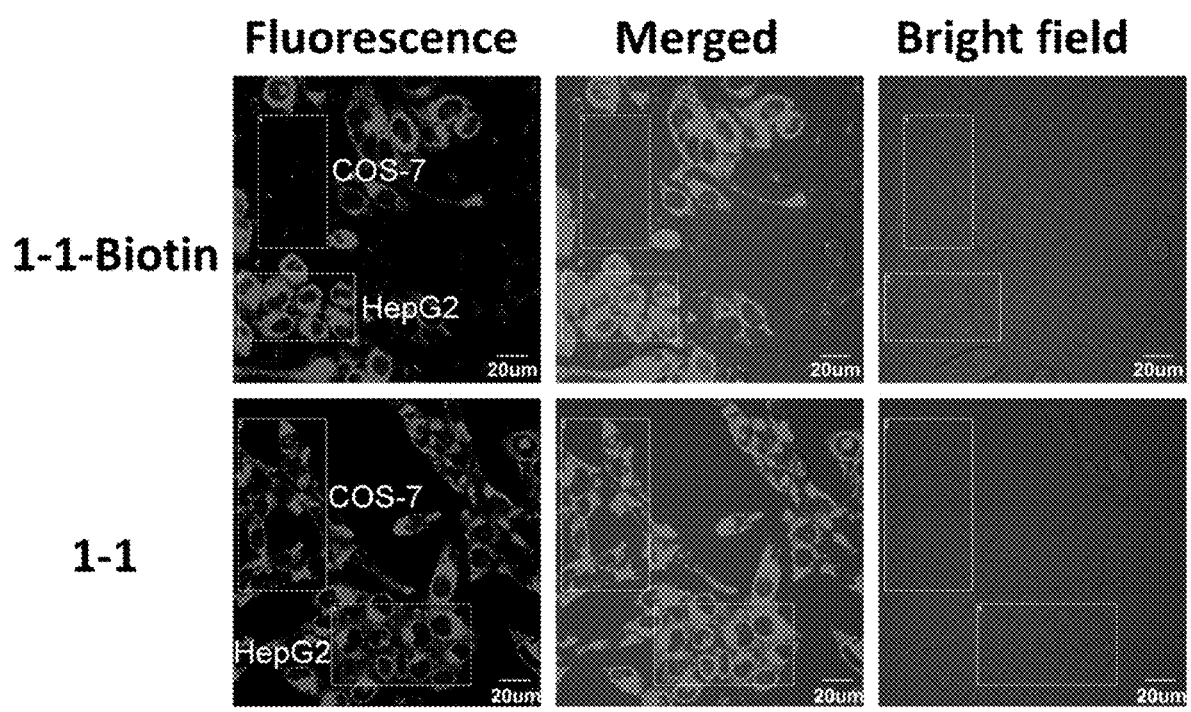
FIG. 12 is the result of in vitro cell selectivity test of the 1-1-biotin which is the derivative of benzophenothiazine linked by Biotin and benzothiazine photosensitizer 1-1. HepG2 and COS-7 are selected as the study subjects. The intensity of red fluorescence represented the level of cell uptake of photosensitizer.

Firstly, HepG2 cells and COS-7 cells are cultured together in a cell culture dish for 24 h, and then 1 μM of 1-1-biotin or 1-1 is added and further incubation for 1 h. After staining, the cells are washed using serum-free medium for three times. Then, 2 mL fresh medium is added, and corresponding fluorescence observation is performed using the laser confocal scanning microscope. The excitation wavelength is 635 nm and the fluorescence receiving channel is 655 nm-755 nm. FIG. 12 shows the corresponding test results. It can be seen from the figure that 1-1 Biotin can specifically target HepG2 cells, while the uptake of 1-1 Biotin in COS-7 cells is very limited. As control, benzothiazine photosensitizer 1-1 does not have such selectivity.

The invention claimed is:
1. A photosensitizer of formula I:

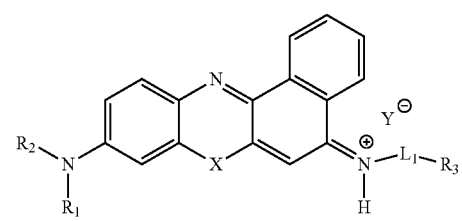

I wherein:

X is Se;

Y is selected from halogen ion, $ClO_4^-$, $PF_6^-$, $BF_4^-$, $CH_3COO^-$, and $OTs^-$;

$R_1$ and $R_2$ are independently selected from H, alkyl, alkoxy, alkylamido, alkyl azide, alkylalkynyl, alkylamino, alkylsulfonyl, alkylhydroxy, and alkylcarboxy;

$R_3$ is selected from H, alkyl, alkoxy, aryloxy, morpholinyl, carbonyl, amido, azido, alkynyl, amino, sulfonic acid, hydroxy and carboxy; and $L_1$ is a linking chain selected from $-(CH_2)_m-$ and $-(CH_2CH_2O)_n-$, m being an integer from 5 to 20, and n being an integer from 2 to 20.

2. The photosensitizer of claim 1, wherein $R_1$ and $R_2$ are independently selected from H, alkyl group of $C_{1-5}$, alkoxy group of $C_{1-5}$, alkyl alkyne group of $C_{2-5}$, alkyl sulfonyl group of $C_{2-6}$, and alkyl azide group of $C_{2-6}$.

3. The photosensitizer of claim 1, wherein the said $R_3$ is selected from amino, carboxyl, hydroxyl, and azido.

4. The photosensitizer of claim 1, wherein m or n are independently 5, 6, 7 or 8.

5. The photosensitizer of claim 1, wherein the said photosensitizer of formula I is 2-1
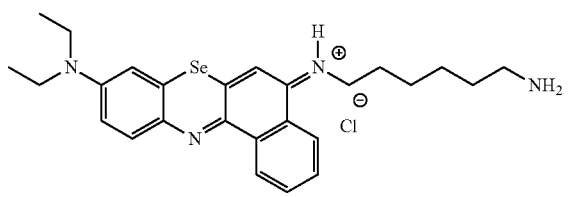

or 2-2
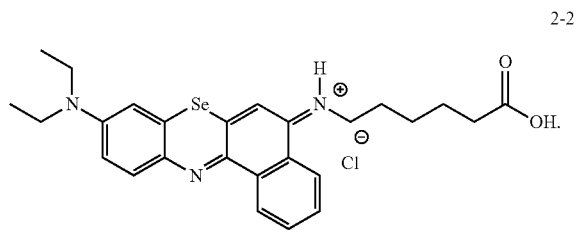

6. A method of treating tumor comprising administering an effective amount of a composition to a subject in need thereof, wherein the composition comprises the photosensitizer of claim 1; and subjecting the composition to light irradiation.

7. A derivative of the photosensitizer of claim 1, having a formula of Formula II:

II
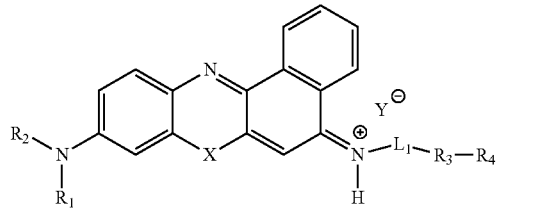

wherein X, Y, $R_1$, $R_2$, $R_3$, and $L_1$ are as defined in claim 1, and $R_4$ is an anticancer and chemotherapy drug molecule or a molecular drug with tumor targeting function.

8. The photosensitizer derivative of claim 7, wherein $R_4$ is selected from a1 to a10:

a1
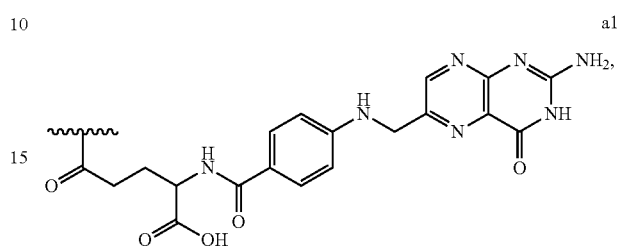

a2
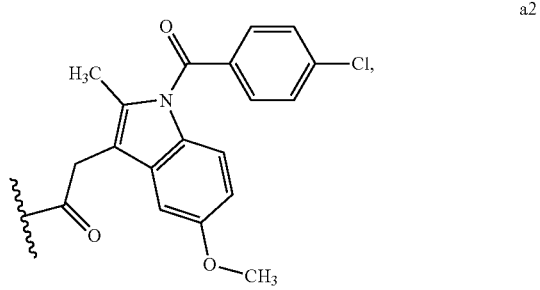

a3
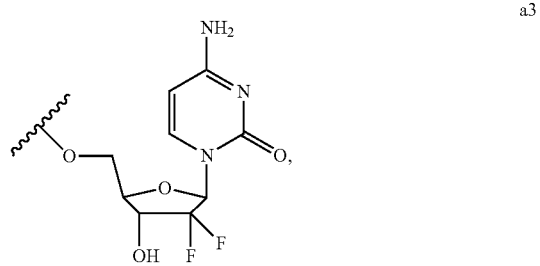

a4
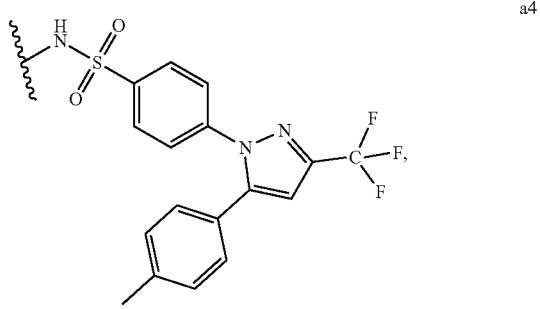

-continued
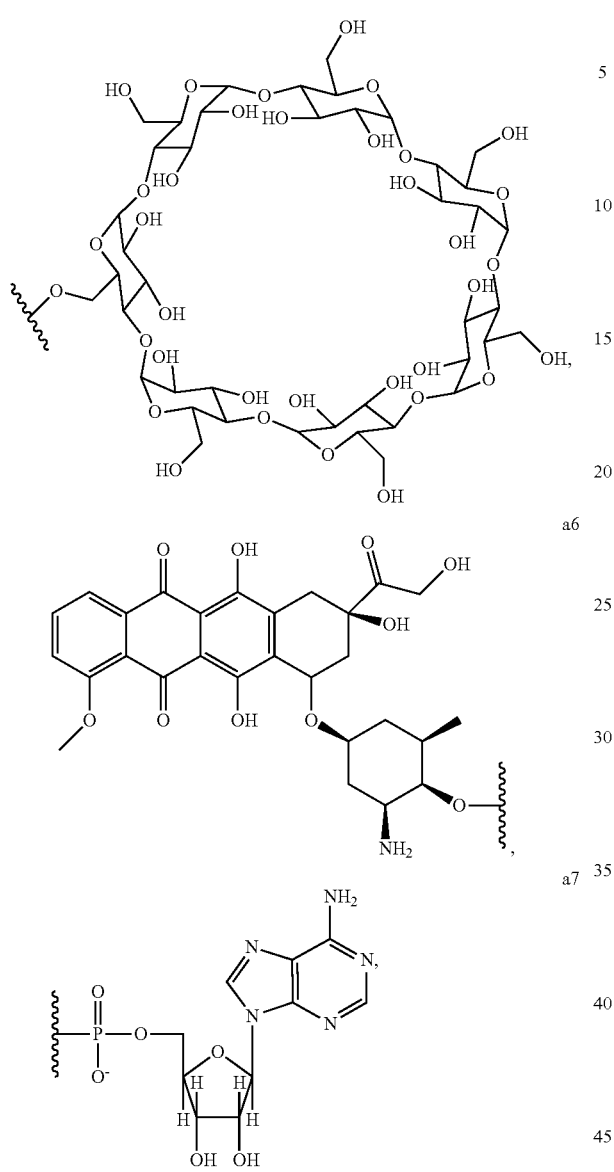
a5
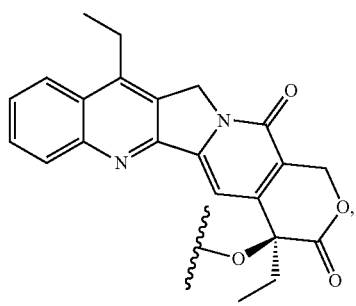
a8
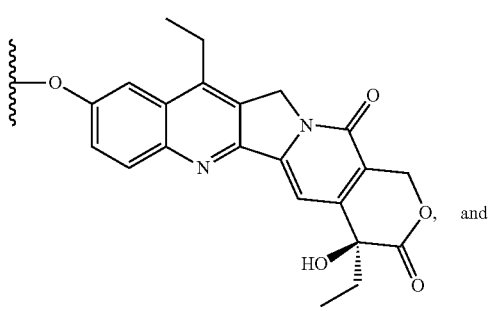
a9
and
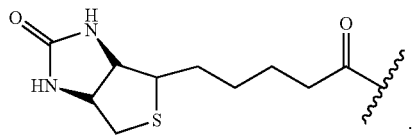
a10
9. The photosensitizer derivative of claim 7 is
1-1-IMC
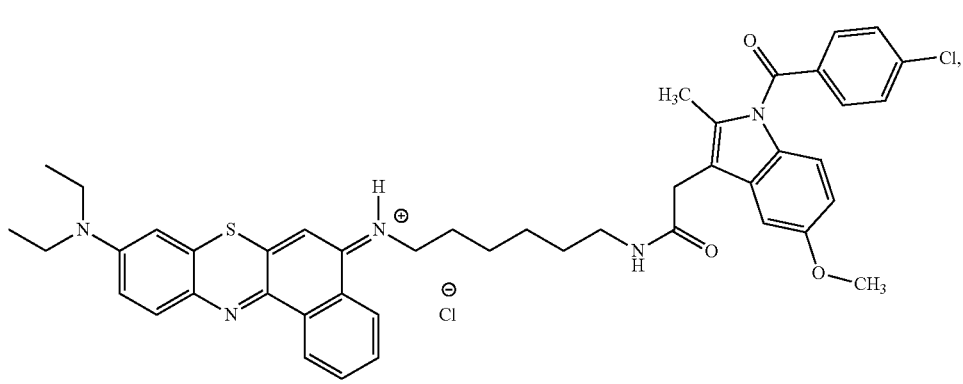

-continued
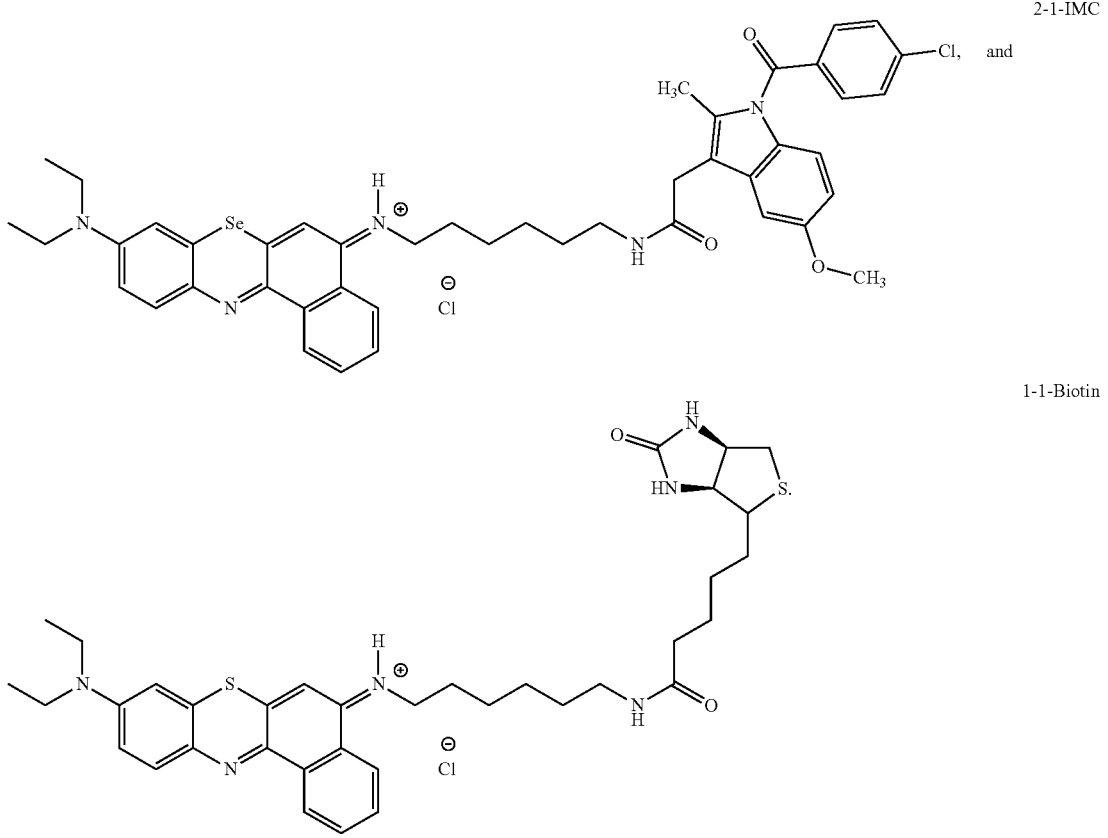
10. A method of treating tumor comprising administering an effective amount of a composition to a subject in need thereof, wherein the composition comprises the photosensitizer derivatives of claim 7; and subjecting the composition to light irradiation.
* * * * *